US012698511B2

(12) United States Patent
Madera et al.

(10) Patent No.: US 12,698,511 B2
(45) Date of Patent: Aug. 4, 2026

(54) CODON-OPTIMIZED NUCLEIC ACID ENCODING SMN1 PROTEIN

(71) Applicant: LIMITED LIABILITY COMPANY "ANABION", Saint Petersburg (RU)

(72) Inventors: Dmitriy Aleksandrovich Madera, Moscow (RU); Pavel Mikhailovich Gershovich, Saint Petersburg (RU); Anna Sergeevna Veselova, Saint Petersburg (RU); Tatiana Evgenievna Shugaeva, Moscow (RU); Maria Andreevna Lomunova, Saint Petersburg (RU); Margarita Aleksandrovna Shkliaeva, Saint Petersburg (RU); Dmitry Valentinovich Morozov, Saint Petersburg (RU)

(73) Assignee: JOINT STOCK COMPANY "BIOCAD", Saint Petersburg (RU)

( * ) Notice: Subject to any disclaimer, the term of this patent is extended or adjusted under 35 U.S.C. 154(b) by 821 days.

(21) Appl. No.: 18/000,612

(22) PCT Filed: Jun. 2, 2021

(86) PCT No.: PCT/RU2021/000238
§ 371 (c)(1),
(2) Date: Dec. 2, 2022

(87) PCT Pub. No.: WO2021/246909
PCT Pub. Date: Dec. 9, 2021

(65) Prior Publication Data
US 2023/0212609 A1     Jul. 6, 2023

(30) Foreign Application Priority Data
Jun. 2, 2020     (RU) ................................. 2020118148

(51) Int. Cl.
*C12N 15/86*     (2006.01)
*C07K 14/47*     (2006.01)

(52) U.S. Cl.
CPC .............. *C12N 15/86* (2013.01); *C07K 14/47* (2013.01); *C12N 2750/14122* (2013.01); *C12N 2750/14143* (2013.01); *C12N 2800/22* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,634,665 A | 1/1987 | Axel et al. |
| 5,179,017 A | 1/1993 | Axel et al. |
| 2016/0066669 A1* | 3/2016 | Wilson .................. A61K 48/00 |

FOREIGN PATENT DOCUMENTS

| | | |
|---|---|---|
| EP | 0323997 A1 | 7/1989 |
| EP | 0173177 B1 | 4/1992 |
| WO | 2017/106354 A1 | 6/2017 |

OTHER PUBLICATIONS

Perez-Martinez et al., "Barriers to non-viral vector mediated gene delivery in the nervous system" Pharm Res (Year: 2011).*
Strokach et al., "Predicting the effect of mutations on protein folding and protein-protein interactions" Computational Methods in Protein Evolution (Year: 2018).*
Szynyogova et al., "survival motor neuron protein is required for normal mouse liver development" Scientific Reports (Year: 2016).*
Wang et al., "available methods for assembling expression cassettes for synthetic biology" Appl Microbiol Biotechnol (Year: 2012).*
International application No. PCT/RU2021/000238 International Search Report dated Oct. 14, 2021.
International application No. PCT/RU2021/000238 Translation of the International Search Report dated Oct. 14, 2021.
International application No. PCT/RU2021/000238 Written Opinion of the International Searching Authority dated Oct. 14, 2021.
Mori S. et al., Two novel adeno-associated viruses from cynomolgus monkey: pseudotyping characterization of capsid protein. Virology. vol. 330, Issue 2, Dec. 20, 2004, pp. 375-383.
Marco A. Passini et al., Translational fidelity of intrathecal delivery of self-complementary AAV9-survival motor neuron 1 for spinal muscular atrophy. Human Gene Therapy. vol. 25, No. 7. Jul. 2014, pp. 619-630.
Lefebvre et al., Identification and characterization of a spinal muscular atrophy-determining gene. Cell. vol. 80, Issue 1, Jan. 13, 1995, pp. 155-165.
Sumner C.J., Therapeutics development for spinal muscular atrophy. NeuroRX (2006) 3: pp. 235-245.
Xie Q. et al. The atomic structure of adeno-associated virus (AAV-2), a vector for human gene therapy. Proc Natl Acad Sci USA, Jul. 22, 2002; 99:10405-10410.
Kudla et al., High Guanine and Cytosine Content Increases mRNA Levels in Mammalian Cells, Jun. 2006, vol. 4, Issue 6, e180, pp. 933-942.
McLaughlin et al., Adeno-associated virus general transduction vectors: analysis of proviral structures. ASM Journals, Journal of Virology. vol. 62, No. 6. (1988). pp. 1963-1973.

(Continued)

*Primary Examiner* — Tracy Vivlemore
*Assistant Examiner* — John David Moore
(74) *Attorney, Agent, or Firm* — Anglehart et al.

(57) ABSTRACT

The present application relates to the fields of genetics, gene therapy, and molecular biology. More specifically, the present invention relates to an isolated codon-optimized nucleic acid that encodes the SMN1 protein (survival motor neuron protein), an expression cassette and a vector based thereon, as well as an AAV9 (adeno-associated virus serotype 9)-based recombinant virus for increasing the expression of the SMN1 gene in target cells, and use thereof.

13 Claims, 3 Drawing Sheets
Specification includes a Sequence Listing.

(56)                 References Cited

OTHER PUBLICATIONS

Yasukazu Nakamura et al., Codon usage tabulated from the international DNA sequence databases; its status 1999, Nucleic Acids Research, vol. 27, Issue 1, Jan. 1, 1999, p. 292, https://doi.org/10.1093/nar/27.1.292.

Zuker algorithm, et al., Optimal computer folding of large RNA sequences using thermodynamics and auxiliary information, Nucleic Acids Research, vol. 9, Issue 1, Jan. 10, 1981, pp. 133-148, doi: 10.1093/nar/9.1.133.

Paul M. Sharp, et al., The codon adaptation index-a measure of directional synonymous codon usage bias, and its potential applications, Nucleic Acids Research, vol. 15, Issue 3, Feb. 11, 1987, pp. 1281-1295, doi: 10.1093/nar/15.3.1281.

High KA et al., rAAV human trial experience. Methods in Molecular Biology (Clifton, N.J.), Jan. 1, 2011, 807:429-457 (Abstract provided).

* cited by examiner

SEQUENCE LISTING

<160> NUMBER OF SEQ ID NOS: 13

<210> SEQ ID NO 1
<211> LENGTH: 294
<212> TYPE: PRT
<213> ORGANISM: Unknown
<220> FEATURE:
<223> OTHER INFORMATION: The amino acid sequence of the SMN1 protein

<400> SEQUENCE: 1

Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
                20                  25                  30

Ile Trp Asp Asp Thr Ala Leu Ile Lys Ala Tyr Asp Lys Ala Val Ala
            35                  40                  45

Ser Phe Lys His Ala Leu Lys Asn Gly Asp Ile Cys Glu Thr Ser Gly
        50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
                100                 105                 110

Ile Ala Ser Ile Asp Phe Lys Arg Glu Thr Cys Val Val Val Tyr Thr
                115                 120                 125

Gly Tyr Gly Asn Arg Glu Glu Gln Asn Leu Ser Asp Leu Leu Ser Pro
        130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
                180                 185                 190

Phe Leu Pro Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro Pro
        210                 215                 220

Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
        260                 265                 270

His Thr Gly Tyr Tyr Met Gly Phe Arg Gln Asn Gln Lys Glu Gly Arg
        275                 280                 285

Cys Ser His Ser Leu Asn
    290

<210> SEQ ID NO 2
<211> LENGTH: 882
<212> TYPE: DNA
<213> ORGANISM: Artificial sequence
<220> FEATURE:
<223> OTHER INFORMATION: Codon-an optimized nucleic acid sequence that
      encodes the SMN1 protein (SMN1 GeneBeam)

<400> SEQUENCE: 2

-continued

```
atggccatga gcagcggcgg cagcggcggc ggcgtgcctg agcaagagga cagcgtgctg    60
ttcagaagag gcaccggcca gagcgacgac agcgacatct gggacgacac cgccctgatc   120
aaggcctacg acaaggccgt ggccagcttc aagcacgccc tgaagaacgg cgacatctgc   180
gagaccagcg gcaagcccaa gaccacccc aagagaaagc ccgccaagaa gaacaagagc    240
cagaagaaga acaccgccgc cagcctgcag cagtggaagg tgggcgacaa gtgcagcgcc   300
atctggagcg aggacggctg catctacccc gccaccatcg ccagcatcga cttcaagaga   360
gagacctgcg tggtggtgta caccggctac ggcaacagag aggagcagaa cctgagcgac   420
ctgctgagcc ccatctgcga ggtggccaac aacatcgagc agaacgccca agagaacgag   480
aacgagagcc aagtgagcac cgacgagagc gagaacagca gaagcccgg caacaagagc     540 gacaacatca gcccaagag cgcccctgg aacagcttcc tgcccctcc ccccctatg       600 cccggcccta gactgggccc tggcaagcct ggcctgaagt tcaacggccc cccccccct     660 cctcctcctc ctcctcctca cctgctgagc tgctggctgc cccccttccc cagcggccct    720
cctatcatcc ctcctccccc ccccatctgc cccgacagcc tggacgacgc cgacgccctg    780
ggcagcatgc tgatcagctg gtacatgagc ggctaccaca ccggctacta catgggcttc    840
agacagaacc agaaggaggg ccggtgcagc cacagcctga ac                       882
```

```
<210> SEQ ID NO 3
<211> LENGTH: 885
<212> TYPE: DNA
<213> ORGANISM: Unknown
<220> FEATURE:
<223> OTHER INFORMATION: The nucleic acid sequence of the wild-type SMN1
      gene (SMN1-WT, SMN1-Wild type)

<400> SEQUENCE: 3
```

```
atggcgatga gcagcggcgg cagtggtggc ggcgtcccgg agcaggagga ttccgtgctg    60
ttccggcgcg gcacaggcca gagcgatgat tctgacattt gggatgatac agcactgata   120
aaagcatatg ataaagctgt ggcttcattt aagcatgctc taaagaatgg tgacatttgt   180
gaaacttcgg gtaaaccaaa aaccacacct aaaagaaaac ctgctaagaa gaataaaagc   240
caaaagaaga atactgcagc ttccttacaa cagtggaaag ttggggacaa atgttctgcc   300
atttggtcag aagacggttg catttaccca gctaccattg cttcaattga ttttaagaga   360
gaaacctgtg ttgtggttta cactggatat ggaaatagag aggagcaaaa tctgtccgat   420
ctactttccc caatctgtga agtagctaat aatatagaac aaaatgctca agagaatgaa   480
aatgaaagcc aagtttcaac agatgaaagt gagaactcca ggtctcctgg aaataaatca   540
gataacatca gcccaaatc tgctccatgg aactcttttc tccctccacc accccccatg    600
ccagggccaa gactgggacc aggaaagcca ggtctaaaat caatggccc accaccgcca     660 ccgccaccac caccacccca cttactatca tgctggctgc ctccatttcc ttctggacca    720
ccaataattc ccccaccacc tcccatatgt ccagattctc ttgatgatgc tgatgctttg    780
ggaagtatgt taatttcatg gtacatgagt ggctatcata ctggctatta tatgggtttc   840
agacaaaatc aaaaagaagg aaggtgctca cattccttaa attaa                    885
```

```
<210> SEQ ID NO 4
<211> LENGTH: 2924
<212> TYPE: DNA
<213> ORGANISM: Artificial sequence
<220> FEATURE:
<223> OTHER INFORMATION: The nucleic acid sequence of the expression
```

-continued cassette (complete)

<400> SEQUENCE: 4

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggccgcac gcgtctagtt attaatagta atcaattacg gggtcattag     180
ttcatagccc atatatggag ttccgcgtta cataacttac ggtaaatggc ccgcctggct     240
gaccgcccaa cgacccccgc ccattgacgt caataatgac gtatgttccc atagtaacgc     300
caatagggac tttccattga cgtcaatggg tggagtattt acggtaaact gcccacttgg     360
cagtacatca agtgtatcat atgccaagta cgccccctat tgacgtcaat gacggtaaat     420
ggcccgcctg gcattatgcc cagtacatga ccttatggga ctttcctact tggcagtaca     480
tctacgtatt agtcatcgct attaccatgg tgatgcggtt ttggcagtac atcaatgggc     540
gtggatagcg gtttgactca cggggatttc caagtctcca ccccattgac gtcaatggga     600
gtttgttttg gcaccaaaat caacgggact ttccaaaatg tcgtaacaac tccgccccat     660
tgacgcaaat gggcggtagg cgtgtacggt gggaggtcta tataagcaga gctcgtttag     720
tgaaccgtca gatcgcctgg agacgccatc cacgctgttt tgacctccat agaagacacc     780
gggaccgatc cagcctccgc ggattcgaat cccggccggg aacggtgcat tggaacgcgg     840
attccccgtg ccaagagtga cgtaagtacc gcctatagag tctataggcc cacaaaaaat     900
gctttcttct tttaatatac tttttttgttt atcttatttc taatactttc cctaatctct     960
ttctttcagg gcaataatga tacaatgtat catgcctctt tgcaccattc taaagaataa    1020
cagtgataat ttctgggtta aggcaatagc aatatttctg catataaata tttctgcata    1080
taaattgtaa ctgatgtaag aggtttcata ttgctaatag cagctacaat ccagctacca    1140
ttctgctttt attttatggt tgggataagg ctggattatt ctgagtccaa gctaggccct    1200
tttgctaatc atgttcatac ctcttatctt cctcccacag ctcctgggca acgtgctggt    1260
ctgtgtgctg gcccatcact ttggcaaaga attgggattc gaacatcgat tgtaattcat    1320
gagccaccat ggccatgagc agcggcggca gcggcggcgg cgtgcctgag caagaggaca    1380
gcgtgctgtt cagaagaggc accggccaga gcgacgacag cgacatctgg gacgacaccg    1440
ccctgatcaa ggcctacgac aaggccgtgg ccagcttcaa gcacgccctg aagaacggcg    1500
acatctgcga gaccagcggc aagcccaaga ccacccccaa gagaaagccc gccaagaaga    1560
acaagagcca gaagaagaac accgccgcca gcctgcagca gtggaaggtg ggcgacaagt    1620
gcagcgccat ctggagcgag gacggctgca tctacccgc caccatcgcc agcatcgact    1680
tcaagagaga gacctgcgtg gtggtgtaca ccggctacgg caacagagag gagcagaacc    1740
tgagcgacct gctgagcccc atctgcgagg tggccaacaa catcgagcag aacgcccaag    1800
agaacgagaa cgagagccaa gtgagcaccg acgagagcga aacagcaga gccccggca    1860 acaagagcga caacatcaag cccaagagcg ccccctggaa cagcttcctg cccctccccc    1920
cccctatgcc cggccctaga ctgggccctg gcaagcctgg cctgaagttc aacggccccc    1980 cccccctcc tcctcctcct cctcctcacc tgctgagctg ctggctgccc cccttcccca    2040
gcggccctcc tatcatccct cctccccccc ccatctgccc cgacagcctg gacgacgccg    2100
acgccctggg cagcatgctg atcagctggt acatgagcgg ctaccacacc ggctactaca    2160
tgggcttcag acagaaccag aaggagggcc ggtgcagcca cagcctgaac tgatctagag    2220
tcgacctgca gaagcttgcc tcgagcagcg ctgctcgaga gatctacggg tggcatccct    2280
```

-continued

```
gtgacccctc cccagtgcct ctcctggccc tggaagttgc cactccagtg cccaccagcc      2340
ttgtcctaat aaaattaagt tgcatcattt tgtctgacta ggtgtccttc tataatatta      2400
tggggtggag gggggtggta tggagcaagg ggcaagttgg gaagacaacc tgtagggcct      2460
gcggggtcta ttgggaacca agctggagtg cagtggcaca atcttggctc actgcaatct      2520
ccgcctcctg ggttcaagcg attctcctgc ctcagcctcc cgagttgttg ggattccagg      2580
catgcatgac caggctcagc taattttttgt ttttttggta gagacggggt ttcaccatat      2640
tggccaggct ggtctccaac tcctaatctc aggtgatcta cccaccttgg cctcccaaat      2700
tgctgggatt acaggcgtga accactgctc ccttccctgt ccttctgatt ttgtaggtaa      2760
ccacgtgcgg accgagcggc cgcaggaacc cctagtgatg gagttggcca ctccctctct      2820
gcgcgctcgc tcgctcactg aggccgggcg accaaaggtc gcccgacgcc cgggctttgc      2880
ccgggcggcc tcagtgagcg agcgagcgcg cagctgcctg cagg                       2924
```

<210> SEQ ID NO 5
<211> LENGTH: 736
<212> TYPE: PRT
<213> ORGANISM: Unknown
<220> FEATURE:
<223> OTHER INFORMATION: The amino acid sequence of the VP1 AAV9 protein

<400> SEQUENCE: 5

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
```

```
                    245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
    305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
    385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
    465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
    545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
    625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670
```

-continued

```
Gln Tyr Ser Thr Gly Gln Val Ser Val Glu Ile Glu Trp Glu Leu Gln
        675             680             685

Lys Glu Asn Ser Lys Arg Trp Asn Pro Glu Ile Gln Tyr Thr Ser Asn
    690             695             700

Tyr Tyr Lys Ser Asn Asn Val Glu Phe Ala Val Asn Thr Glu Gly Val
705             710             715             720

Tyr Ser Glu Pro Arg Pro Ile Gly Thr Arg Tyr Leu Thr Arg Asn Leu
            725             730             735
```

<210> SEQ ID NO 6
<211> LENGTH: 599
<212> TYPE: PRT
<213> ORGANISM: Unknown
<220> FEATURE:
<223> OTHER INFORMATION: The amino acid sequence of the VP2 AAV9 protein

<400> SEQUENCE: 6

```
Thr Ala Pro Gly Lys Lys Arg Pro Val Glu Gln Ser Pro Gln Glu Pro
1               5               10              15

Asp Ser Ser Ala Gly Ile Gly Lys Ser Gly Ala Gln Pro Ala Lys Lys
            20              25              30

Arg Leu Asn Phe Gly Gln Thr Gly Asp Thr Glu Ser Val Pro Asp Pro
        35              40              45

Gln Pro Ile Gly Glu Pro Pro Ala Ala Pro Ser Gly Val Gly Ser Leu
    50              55              60

Thr Met Ala Ser Gly Gly Gly Ala Pro Val Ala Asp Asn Asn Glu Gly
65              70              75              80

Ala Asp Gly Val Gly Ser Ser Ser Gly Asn Trp His Cys Asp Ser Gln
            85              90              95

Trp Leu Gly Asp Arg Val Ile Thr Thr Ser Thr Arg Thr Trp Ala Leu
        100             105             110

Pro Thr Tyr Asn Asn His Leu Tyr Lys Gln Ile Ser Asn Ser Thr Ser
        115             120             125

Gly Gly Ser Ser Asn Asp Asn Ala Tyr Phe Gly Tyr Ser Thr Pro Trp
    130             135             140

Gly Tyr Phe Asp Phe Asn Arg Phe His Cys His Phe Ser Pro Arg Asp
145             150             155             160

Trp Gln Arg Leu Ile Asn Asn Asn Trp Gly Phe Arg Pro Lys Arg Leu
            165             170             175

Asn Phe Lys Leu Phe Asn Ile Gln Val Lys Glu Val Thr Asp Asn Asn
        180             185             190

Gly Val Lys Thr Ile Ala Asn Asn Leu Thr Ser Thr Val Gln Val Phe
    195             200             205

Thr Asp Ser Asp Tyr Gln Leu Pro Tyr Val Leu Gly Ser Ala His Glu
    210             215             220

Gly Cys Leu Pro Pro Phe Pro Ala Asp Val Phe Met Ile Pro Gln Tyr
225             230             235             240

Gly Tyr Leu Thr Leu Asn Asp Gly Ser Gln Ala Val Gly Arg Ser Ser
        245             250             255

Phe Tyr Cys Leu Glu Tyr Phe Pro Ser Gln Met Leu Arg Thr Gly Asn
        260             265             270

Asn Phe Gln Phe Ser Tyr Glu Phe Glu Asn Val Pro Phe His Ser Ser
    275             280             285

Tyr Ala His Ser Gln Ser Leu Asp Arg Leu Met Asn Pro Leu Ile Asp
    290             295             300
```

-continued

```
Gln Tyr Leu Tyr Tyr Leu Ser Lys Thr Ile Asn Gly Ser Gly Gln Asn
305             310              315              320

Gln Gln Thr Leu Lys Phe Ser Val Ala Gly Pro Ser Asn Met Ala Val
                325              330              335

Gln Gly Arg Asn Tyr Ile Pro Gly Pro Ser Tyr Arg Gln Gln Arg Val
            340              345              350

Ser Thr Thr Val Thr Gln Asn Asn Ser Glu Phe Ala Trp Pro Gly
        355              360              365

Ala Ser Ser Trp Ala Leu Asn Gly Arg Asn Ser Leu Met Asn Pro Gly
        370              375              380

Pro Ala Met Ala Ser His Lys Glu Gly Glu Asp Arg Phe Phe Pro Leu
385              390              395              400

Ser Gly Ser Leu Ile Phe Gly Lys Gln Gly Thr Gly Arg Asp Asn Val
            405              410              415

Asp Ala Asp Lys Val Met Ile Thr Asn Glu Glu Glu Ile Lys Thr Thr
            420              425              430

Asn Pro Val Ala Thr Glu Ser Tyr Gly Gln Val Ala Thr Asn His Gln
        435              440              445

Ser Ala Gln Ala Gln Ala Gln Thr Gly Trp Val Gln Asn Gln Gly Ile
        450              455              460

Leu Pro Gly Met Val Trp Gln Asp Arg Asp Val Tyr Leu Gln Gly Pro
465              470              475              480

Ile Trp Ala Lys Ile Pro His Thr Asp Gly Asn Phe His Pro Ser Pro
            485              490              495

Leu Met Gly Gly Phe Gly Met Lys His Pro Pro Pro Gln Ile Leu Ile
            500              505              510

Lys Asn Thr Pro Val Pro Ala Asp Pro Pro Thr Ala Phe Asn Lys Asp
        515              520              525

Lys Leu Asn Ser Phe Ile Thr Gln Tyr Ser Thr Gly Gln Val Ser Val
        530              535              540

Glu Ile Glu Trp Glu Leu Gln Lys Glu Asn Ser Lys Arg Trp Asn Pro
545              550              555              560

Glu Ile Gln Tyr Thr Ser Asn Tyr Tyr Lys Ser Asn Asn Val Glu Phe
            565              570              575

Ala Val Asn Thr Glu Gly Val Tyr Ser Glu Pro Arg Pro Ile Gly Thr
            580              585              590

Arg Tyr Leu Thr Arg Asn Leu
        595
```

```
<210> SEQ ID NO 7
<211> LENGTH: 534
<212> TYPE: PRT
<213> ORGANISM: Unknown
<220> FEATURE:
<223> OTHER INFORMATION: The amino acid sequence of the VP3 AAV9 protein

<400> SEQUENCE: 7
```

```
Met Ala Ser Gly Gly Gly Ala Pro Val Ala Asp Asn Asn Glu Gly Ala
1               5               10              15

Asp Gly Val Gly Ser Ser Ser Gly Asn Trp His Cys Asp Ser Gln Trp
            20              25              30

Leu Gly Asp Arg Val Ile Thr Thr Ser Thr Arg Thr Trp Ala Leu Pro
        35              40              45

Thr Tyr Asn Asn His Leu Tyr Lys Gln Ile Ser Asn Ser Thr Ser Gly
    50              55              60
```

-continued

```
Gly Ser Ser Asn Asp Asn Ala Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Asn
            100                 105                 110

Phe Lys Leu Phe Asn Ile Gln Val Lys Glu Val Thr Asp Asn Asn Gly
        115                 120                 125

Val Lys Thr Ile Ala Asn Asn Leu Thr Ser Thr Val Gln Val Phe Thr
    130                 135                 140

Asp Ser Asp Tyr Gln Leu Pro Tyr Val Leu Gly Ser Ala His Glu Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asp Gly Ser Gln Ala Val Gly Arg Ser Ser Phe
            180                 185                 190

Tyr Cys Leu Glu Tyr Phe Pro Ser Gln Met Leu Arg Thr Gly Asn Asn
        195                 200                 205

Phe Gln Phe Ser Tyr Glu Phe Glu Asn Val Pro Phe His Ser Ser Tyr
    210                 215                 220

Ala His Ser Gln Ser Leu Asp Arg Leu Met Asn Pro Leu Ile Asp Gln
225                 230                 235                 240

Tyr Leu Tyr Tyr Leu Ser Lys Thr Ile Asn Gly Ser Gly Gln Asn Gln
                245                 250                 255

Gln Thr Leu Lys Phe Ser Val Ala Gly Pro Ser Asn Met Ala Val Gln
            260                 265                 270

Gly Arg Asn Tyr Ile Pro Gly Pro Ser Tyr Arg Gln Gln Arg Val Ser
        275                 280                 285

Thr Thr Val Thr Gln Asn Asn Asn Ser Glu Phe Ala Trp Pro Gly Ala
    290                 295                 300

Ser Ser Trp Ala Leu Asn Gly Arg Asn Ser Leu Met Asn Pro Gly Pro
305                 310                 315                 320

Ala Met Ala Ser His Lys Glu Gly Glu Asp Arg Phe Phe Pro Leu Ser
                325                 330                 335

Gly Ser Leu Ile Phe Gly Lys Gln Gly Thr Gly Arg Asp Asn Val Asp
            340                 345                 350

Ala Asp Lys Val Met Ile Thr Asn Glu Glu Glu Ile Lys Thr Thr Asn
        355                 360                 365

Pro Val Ala Thr Glu Ser Tyr Gly Gln Val Ala Thr Asn His Gln Ser
    370                 375                 380

Ala Gln Ala Gln Ala Gln Thr Gly Trp Val Gln Asn Gln Gly Ile Leu
385                 390                 395                 400

Pro Gly Met Val Trp Gln Asp Arg Asp Val Tyr Leu Gln Gly Pro Ile
                405                 410                 415

Trp Ala Lys Ile Pro His Thr Asp Gly Asn Phe His Pro Ser Pro Leu
            420                 425                 430

Met Gly Gly Phe Gly Met Lys His Pro Pro Gln Ile Leu Ile Lys
        435                 440                 445

Asn Thr Pro Val Pro Ala Asp Pro Pro Thr Ala Phe Asn Lys Asp Lys
    450                 455                 460

Leu Asn Ser Phe Ile Thr Gln Tyr Ser Thr Gly Gln Val Ser Val Glu
465                 470                 475                 480
```

```
Ile Glu Trp Glu Leu Gln Lys Glu Asn Ser Lys Arg Trp Asn Pro Glu
                485                 490                 495

Ile Gln Tyr Thr Ser Asn Tyr Tyr Lys Ser Asn Asn Val Glu Phe Ala
            500                 505                 510

Val Asn Thr Glu Gly Val Tyr Ser Glu Pro Arg Pro Ile Gly Thr Arg
        515                 520                 525

Tyr Leu Thr Arg Asn Leu
    530
```

<210> SEQ ID NO 8
<211> LENGTH: 130
<212> TYPE: DNA
<213> ORGANISM: Unknown
<220> FEATURE:
<223> OTHER INFORMATION: Left (first) ITR (inverted end repeats)

<400> SEQUENCE: 8

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct                                                            130
```

<210> SEQ ID NO 9
<211> LENGTH: 304
<212> TYPE: DNA
<213> ORGANISM: Unknown
<220> FEATURE:
<223> OTHER INFORMATION: CMV (Cytomegalovirus) Enhancer

<400> SEQUENCE: 9

```
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta     240
catgacctta tgggactttc ctacttggca gtacatctac gtattagtca tcgctattac     300
catg                                                                  304
```

<210> SEQ ID NO 10
<211> LENGTH: 204
<212> TYPE: DNA
<213> ORGANISM: Unknown
<220> FEATURE:
<223> OTHER INFORMATION: CMV (Cytomegalovirus) promoter

<400> SEQUENCE: 10

```
gtgatgcggt tttggcagta catcaatggg cgtggatagc ggtttgactc acggggattt      60
ccaagtctcc accccattga cgtcaatggg agtttgtttt ggcaccaaaa tcaacgggac     120
tttccaaaat gtcgtaacaa ctccgcccca ttgacgcaaa tgggcggtag cgtgtacgg     180 tgggaggtct atataagcag agct                                            204
```

<210> SEQ ID NO 11
<211> LENGTH: 493
<212> TYPE: DNA
<213> ORGANISM: Unknown
<220> FEATURE:
<223> OTHER INFORMATION: Intron of the hBG1 gene (hemoglobin gamma-1
      subunit)

<400> SEQUENCE: 11

-continued

```
cgaatcccgg ccgggaacgg tgcattggaa cgcggattcc ccgtgccaag agtgacgtaa      60
gtaccgccta tagagtctat aggcccacaa aaaatgcttt cttcttttaa tatacttttt     120
tgtttatctt atttctaata ctttccctaa tctctttctt tcagggcaat aatgatacaa     180
tgtatcatgc ctctttgcac cattctaaag aataacagtg ataatttctg ggttaaggca     240
atagcaatat ttctgcatat aaatatttct gcatataaat tgtaactgat gtaagaggtt     300
tcatattgct aatagcagct acaatccagc taccattctg cttttatttt atggttggga     360
taaggctgga ttattctgag tccaagctag gcccttttgc taatcatgtt catacctctt     420
atcttcctcc cacagctcct gggcaacgtg ctggtctgtg tgctggccca tcactttggc     480
aaagaattgg gat                                                        493
```

<210> SEQ ID NO 12
<211> LENGTH: 479
<212> TYPE: DNA
<213> ORGANISM: Unknown
<220> FEATURE:
<223> OTHER INFORMATION: hGH1 polyadenylation signal (polyadenylation
      signal(poly (A)) of Human Growth Hormone)

<400> SEQUENCE: 12

```
acgggtggca tccctgtgac ccctccccag tgcctctcct ggccctggaa gttgccactc      60
cagtgcccac cagccttgtc ctaataaaat taagttgcat cattttgtct gactaggtgt     120
ccttctataa tattatgggg tggaggggggg tggtatggag caagggggcaa gttgggaaga     180 caacctgtag ggcctgcggg gtctattggg aaccaagctg gagtgcagtg gcacaatctt     240
ggctcactgc aatctccgcc tcctgggttc aagcgattct cctgcctcag cctcccgagt     300
tgttgggatt ccaggcatgc atgaccaggc tcagctaatt tttgtttttt tggtagagac     360
ggggtttcac catattggcc aggctggtct ccaactccta atctcaggtg atctacccac     420
cttggcctcc caaattgctg ggattacagg cgtgaaccac tgctcccttc cctgtcctt     479
```

<210> SEQ ID NO 13
<211> LENGTH: 141
<212> TYPE: DNA
<213> ORGANISM: Unknown
<220> FEATURE:
<223> OTHER INFORMATION: Right (second) ITR

<400> SEQUENCE: 13

```
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag ctgcctgcag g                                               141
```

CODON-OPTIMIZED NUCLEIC ACID ENCODING SMN1 PROTEIN

FIELD OF INVENTION

The present application relates to the fields of genetics, gene therapy, and molecular biology. More specifically, the present invention relates to an isolated codon-optimized nucleic acid that encodes the SMN1 protein (survival motor neuron protein), an expression cassette and a vector based thereon, as well as an AAV9 (adeno-associated virus serotype 9)-based recombinant virus for increasing the expression of the SMN1 gene in target cells, and use thereof.

BACKGROUND OF INVENTION

Spinal muscular atrophy (SMA) is an autosomal recessive neuromuscular disorder caused by mutations in the survival motor neuron 1 (SMN1) gene and loss of encoded SMN protein (Lefebvre et al., Cell (1995) 80:155-165). The lack of SMN results in motor neuron degeneration in the ventral (anterior) horn of the spinal cord, which leads to weakness of the proximal muscles responsible for crawling, walking, neck movement and swallowing, and the involuntary muscles that control breathing and coughing (Sumner C. J., NeuroRx (2006) 3:235-245). Consequently, SMA patients are susceptible to pneumonia and other pulmonary problems such as restrictive lung disease.

Gene therapy is a promising approach to treating spinal muscular atrophy (SMA).

Adeno-associated virus (AAV) vectors are considered effective in CNS gene therapy because they have suitable toxicity and immunogenicity profiles, they may be used in nerve cell transduction, and they are able to mediate long-term expression in the CNS.

Adeno-associated virus (AAV) is a small (20 n), independent replication-defective, nonenveloped virus. Many different AAV serotypes have been described in human and primates. The adeno-associated virus genome is composed of (+ or –) single-stranded DNA (ssDNA) being about 4,700 nucleotides long. The genomic DNA has terminal inverted repeats (ITRs) at the ends. The genome comprises two open reading frames (ORFs), Rep and Cap comprising several alternative reading frames encoding various protein products. The rep products are essential for AAV replication, whereas three capsid proteins (VP1, VP2, and VP3), along with other alternative products, are encoded by the Cap gene. VP1, VP2, and VP3 are present at 1:1:10 ratio to form an icosahedral capsid (Xie Q. et al. The atomic structure of adeno-associated virus (AAV-2), a vector for human gene therapy. Proc Natl Acad Sci USA, 2002; 99:10405-10410). During recombinant AAV (rAAV) vector production, an expression cassette flanked by ITR is packaged into an AAV capsid. The genes required for AAV replication are not included in the cassette. Recombinant AAV is considered to be one of the safest and most widely used viral vectors for in vivo gene transfer. Vectors can infect cells of multiple tissue types to provide strong and sustained transgene expression. They are also non-pathogenic, and have a low immunogenicity profile (High K A et al., "rAAV human trial experience" Methods Mol Biol. 2011; 807:429-57).

One of the urgent purposes of research in the area of development of effective gene therapy is codon optimization of genes of interest in vectors to achieve the maximum level of expression of the genes of interest, which, in turn, will allow using lower doses of the vector to achieve a significant effect.

One of the properties of the genetic code is degeneracy, i.e. the ability of different codons (trinucleotides) to encode the same amino acid. Such codons that are translated to the same amino acid are called synonymous codons. In natural sequences, one of the synonymous codons is selected randomly in the course of evolution, but the frequencies of usage of synonymous codons are different: each amino acid has more and less preferred ones. Codon optimization is a widely used technique to amplify the production of protein molecules, which provides a rational mapping of one of suitable synonymous codons to each amino acid in a protein sequence. One of the common principles of codon optimization involves the usage of the most frequent codons, whereas other approaches were introduced later, such as harmonization (reproduction of distribution of codon usage frequencies), but they do not always increase productivity. In addition to codon frequencies, the sequence GC content (ratio of guanine and cytosine to the total length of the sequence) may affect the production efficiency, in particular, it was shown that high GC content is associated with increased mRNA levels in mammalian cells Grzegorz Kudla ET AL., High Guanine and Cytosine Content Increases mRNA Levels in Mammalian Cells, June 2006, Volume 4, Issue 6, e180, pp. 933-942). It is further worth noting that stable secondary structure elements of mRNA, i.e. those having a low free folding energy, may reduce the efficiency.

Different variants of codon-optimization of the sequence of a gene of interest may lead to the following (as compared to a wild-type gene):

a) expression levels of the genes of interest will be slightly increased;

b) expression levels of the genes of interest will be significantly increased;

c) expression levels of the genes of interest will remain approximately at the same level;

d) expression levels of the genes of interest will be lowered.

Thus, there is a need for a codon-optimized sequence of the SMN1 gene to increase the expression of the SMN1 gene in target cells.

It was found that the codon-optimized sequence of SMN1 (SMN1-GeneBeam (or abbreviated as SMN1-GB)), which has the nucleotide sequence of SEQ ID NO: 2, surprisingly increases the transcription of the SMN1 gene by more than 3 times, that is, surprisingly increases the mRNA copy number of SMN1-GeneBeam by more than 3 times as compared to SMN1-WT (wild type), which, in turn, leads to a significant increase in the expression of the SMN1 gene and, accordingly, the SMN protein.

Brief Description of Invention

In one aspect, the present invention relates to an isolated codon-optimized nucleic acid that encodes the SMN1 protein (survival motor neuron protein) with SEQ ID NO: 1, and includes the nucleic acid sequence of SEQ ID NO: 2.

In one aspect, the present invention relates to an expression cassette that includes the above codon-optimized nucleic acid.

In some embodiments, the expression cassette includes the following elements in the 5'-end to 3'-end direction:

a left (first) ITR (inverted terminal repeats);

a CMV (cytomegalovirus) enhancer;

a CMV (cytomegalovirus) promoter;

an intron of the hBG1 gene (hemoglobin subunit gamma 1 gene) the above codon-optimized nucleic acid of the SMN1 gene;

an hGH1 polyadenylation signal (human growth hormone gene polyadenylation signal) a right (second) ITR.

In some embodiments, the expression cassette includes a nucleic acid with the sequence of SEQ ID NO: 4.

In one aspect, the present invention relates to an expression vector that includes the above codon-optimized nucleic acid or the above cassette.

In one aspect, the present invention relates to an AAV9 (adeno-associated virus serotype 9)-based recombinant virus for increasing the expression of the SMN1 gene in target cells, which includes a capsid and the above expression cassette.

In some embodiments, the AAV9-based recombinant virus has a capsid that includes the AAV9 protein VP1.

In some embodiments, the AAV9-based recombinant virus has a capsid that includes the AAV9 protein VP1 having the amino acid sequence of SEQ ID NO: 5.

In some embodiments, the AAV9-based recombinant virus has a capsid that includes the AAV9 protein VP1 having the amino acid sequence of SEQ ID NO: 5 with one or more point mutations.

In some embodiments, the AAV9-based recombinant virus has a capsid that includes the AAV9 protein VP1 having the amino acid sequence of SEQ ID NO: 5 or the amino acid sequence of SEQ ID NO: 5 with one or more point mutations, and the expression cassette includes the following elements in the 5'-end to 3'-end direction:

a CMV enhancer;
a CMV promoter;
an intron of the hBG1 gene;
the above codon-optimized nucleic acid of the SMN1 gene;
an hGH1 polyadenylation signal;
a right ITR.

In some embodiments, the AAV9-based recombinant virus has a capsid that includes the AAV9 protein VP1 having the amino acid sequence of SEQ ID NO: 5 or the amino acid sequence of SEQ ID NO: 5 with one or more point mutations, and the expression cassette comprises a nucleic acid with SEQ ID NO: 4.

In one aspect, the present invention relates to a pharmaceutical composition for delivering the SMN1 gene to target cells, which includes the above AAV9-based recombinant virus in combination with one or more pharmaceutically acceptable excipients.

In one aspect, the present invention relates to the use of the above AAV9-based recombinant virus or the above composition to deliver the SMN1 gene to target cells.

DEFINITIONS AND GENERAL METHODS

Figure 1:
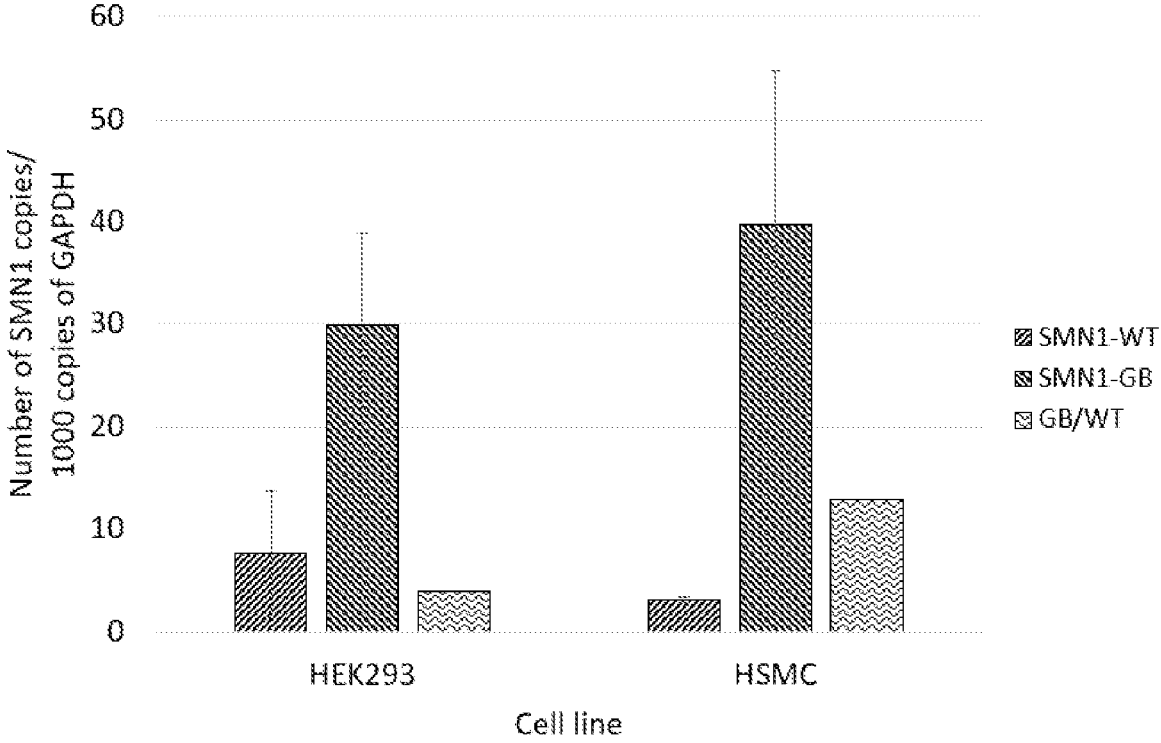
FIG. 1. SMN1 expression at the mRNA level following transfection. HEK293 cells and HSMCs were transfected with 5 μg of plasmids pAAV-SMN1-WT and pAAV-SMN1-GB (encoding the SMN1 gene without codon optimization and with codon optimization according to the GeneBeam algorithm). After 72 hours, the copy number of the SMN1 gene in each sample was determined by quantitative PCR (n=3). The copy number of the GAPDH household gene was also determined. All obtained levels for SMN1 were normalized to 10,000 copies of the GAPDH gene in each sample. Provided is the data on the normalized average copy number of SMN1-WT, SMN-GB for both cell lines, with the indication of a standard deviation. Further provided is the ratio of the normalized copy number of SMN1-GB and SMN1-WT in each line.

Unless defined otherwise, all technical and scientific terms used herein have the same meaning as is commonly understood by one of ordinary skill in the art.

Further, unless otherwise required by context, singular terms shall include pluralities and plural terms shall include the singular. Typically, the classification and methods of cell culture, molecular biology, immunology, microbiology, genetics, analytical chemistry, organic synthesis chemistry, medical and pharmaceutical chemistry, as well as hybridization and chemistry of protein and nucleic acids described herein are well known and widely used by those skilled in the art. Enzyme reactions and purification methods are performed according to the manufacturer's guidelines, as is common in the art, or as described herein.

"Isolated" means altered or removed from the natural state. For example, a nucleic acid or a peptide naturally present in an animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a genetically modified cell.

The terms "naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

The term "genome" refers to the complete genetic material of an organism.

As used in the present description and claims that follow, unless otherwise dictated by the context, the words "include" and "comprise," or variations thereof such as "having," "includes", "including", "comprises," or "comprising," will be understood to imply the inclusion of a stated integer or group of integers but not the exclusion of any other integer or group of integers.

Protein (Peptide)

As used in the present description, the terms "peptide", "polypeptide" and "protein" are used interchangeably, and they refer to a compound consisting of amino acid residues that are covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used in the present description, the term refers to both short chains, which also commonly are referred to in the art, for example, as peptides, oligopeptides and oligomers, and to longer chains, which generally are referred to in the art as proteins, of which there are many types. "Polypeptides" include, inter alia, for example, biologically active fragments, substantially homologous polypeptides, oligopeptides, homodimers, heterodimers, variants of polypeptides, modified polypeptides, derivatives, analogs, fusion proteins. The polypeptides include natural peptides, recombinant peptides, synthetic peptides, or a combination thereof.

Nucleic Acid Molecules

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, determining a fragment or a region of a nucleic acid, containing unnatural nucleotides or not, and being either a double-stranded DNA or RNA, a single-stranded DNA or RNA, or transcription products of said DNAs.

One skilled in the art has the general knowledge that nucleic acids are polynucleotides that can be hydrolyzed to monomeric "nucleotides". Monomeric nucleotides can be hydrolyzed into nucleosides. As used in the present description, polynucleotides include, as non-limiting examples, all nucleic acid sequences which are obtained by any means available in the art, including, as non-limiting examples, recombinant means, i.e. the cloning of nucleic acid sequences from a recombinant library or a cell genome, using ordinary cloning technology and PCR and the like, and by synthetic means.

It should also be noted here that the present invention does not relate to nucleotide sequences in their natural chromosomal environment, i.e. in a natural state. The sequences of the present invention have been isolated and/or purified, i.e. they were sampled directly or indirectly, for example by a copy, their environment having been at least partially modified. Thus, isolated nucleic acids obtained by recombinant genetics, by means, for example, of host cells, or obtained by chemical synthesis should also be mentioned here.

An "isolated" nucleic acid molecule is one which is identified and separated from at least one nucleic acid molecule-impurity, which the former is typically bound to in the natural source of nuclease nucleic acid. An isolated nucleic acid molecule is different from the form or set in which it is found under natural conditions. Thus, an isolated nucleic acid molecule is different from a nucleic acid molecule that exists in cells under natural conditions. An isolated nucleic acid molecule however includes a nucleic acid molecule located in cells in which the nuclease is normally expressed, for example, if the nucleic acid molecule has a chromosomal localization that is different from its localization in cells under natural conditions.

Unless otherwise indicated, the term nucleotide sequence encompasses its complement. Thus, a nucleic acid having a particular sequence should be understood as one which encompasses the complementary strand thereof with the complementary sequence thereof.

The terms "transformation," "transfection," and "transduction" refer to any method or means by which a nucleic acid is introduced into a cell or host organism, and may be used interchangeably to convey the same meaning. Such methods include, but are not limited to, transfection, electroporation, microinjection, infection, PEG-fusion, and the like.

Adeno-Associated Virus (AAV)

Viruses of the Parvoviridae family are small DNA-containing animal viruses. The Parvoviridae family may be divided into two subfamilies: the Parvovirinae, which members infect vertebrates, and the Densovirinae, which members infect insects. By 2006, there have been 11 serotypes of adeno-associated virus described (Mori, S. ET AL., 2004, Two novel adeno-associated viruses from cynomolgus monkey: pseudotyping characterization of capsid protein, Virology, T. 330 (2): 375-83). All of the known serotypes can infect cells from multiple tissue types. Tissue specificity is determined by the capsid protein serotype; therefore, the adeno-associated virus-based vectors are constructed by assigning the desired serotype. Further information on parvoviruses and other members of the Parvoviridae is described in the literature (Kenneth I. Berns, Parvoviridae: The Viruses and Their Replication, Chapter 69 in Fields Virology (3d Ed. 1996)).

The genomic organization of all known AAV serotypes is very similar. The genome of AAV is a linear, single-stranded DNA molecule that is less than about 5000 nucleotides (nt) in length. Inverted terminal repeats (ITRs) flank the unique coding nucleotide sequences of replication of non-structural proteins (Rep) and structural proteins (Cap). The Cap gene encodes the VP proteins (VP1, VP2, and VP3) which form the capsid. The terminal 145 nucleotides are self-complementary and are organized such that an energetically stable intramolecular duplex forming a T-shaped hairpin may be formed. Such hairpin structures function as an origin for viral DNA replication, serving as primers for the cellular DNA polymerase complex. Following wild-type AAV (wtAAV) infection in mammalian cells, the Rep genes (e.g. Rep78 and Rep52) are expressed using the P5 promoter and the P19 promoter, respectively, and the both Rep proteins have a certain function in the replication of the viral genome. A splicing event in the Rep open reading frame (Rep ORF) results in the expression of actually four Rep proteins (e.g. Rep78, Rep68, Rep52, and Rep40). However, it has been shown that the unspliced mRNA encoding Rep78 and Rep52 proteins is sufficient for AAV vector production in mammalian cells.

Vector

The term "vector" as used herein means a nucleic acid molecule capable of transporting another nucleic acid to which it has been linked.

The terms "infection unit (iu)," "infectious particle," or "replication unit," as used in reference to a viral titer, refer to the number of infectious recombinant AAV vector particles as measured by the infectious center assay, also known as replication center assay, as described, for example, in McLaughlin et al., J. Virol. (1988) 62:1963-1973.

The term "heterologous" as it relates to nucleic acid sequences such as coding sequences and regulatory sequences, denotes sequences that are not normally joined together, and/or are not normally associated with a particular cell. Thus, a "heterologous" region of a nucleic acid construct or a vector is a fragment of nucleic acid within or attached to another nucleic acid molecule that is not found in association with the other molecule in nature. For example, a heterologous region of a nucleic acid construct may include a coding sequence flanked by sequences not found in association with the coding sequence in nature.

Another example of a heterologous coding sequence is a construct where the coding sequence itself is not found in nature (e.g. synthetic sequences having codons different from the native gene).

As used in the present description, the term "expression" is defined as the transcription and/or translation of a particular nucleotide sequence driven by its promoter.

Use

"Gene therapy" is the insertion of genes into subject's cells and/or tissues to treat a disease, typically hereditary diseases, in which a defective mutant allele is replaced with a functional one.

"Treat", "treatment" and "therapy" refer to a method of alleviating or abrogating a biological disorder and/or at least one of attendant symptoms thereof. As used herein, to "alleviate" a disease, disorder or condition means reducing the severity and/or occurrence frequency of the symptoms of a disease, disorder, or condition. Further, references herein to "treatment" include references to curative, palliative and prophylactic treatment.

In one aspect, the subject of treatment, or patient, is a mammal, preferably a human subject. Said subject may be either male or female, of any age.

The term "disorder" means any condition that would benefit from treatment according to the present invention. This includes chronic and acute disorders or diseases including those pathological conditions that predispose the mammal to the disorder in question.

"Disease" is a state of health of an animal where the animal cannot maintain homeostasis, and where if the disease is not ameliorated then the animal's health continues to deteriorate.

The terms "subject," "patient," "individual," and the like are used interchangeably in the present description, and they refer to any animal amenable to the methods described in the present description. In certain non-limiting embodiments, the subject, patient or individual is a human.

"Therapeutically effective amount" refers to that amount of the therapeutic agent being administered during treatment which will relieve to some extent one or more of the symptoms of the disease being treated.

DETAILED DESCRIPTION OF INVENTION

Codon-Optimized Nucleic Acid

In one aspect, the present invention relates to an isolated codon-optimized nucleic acid that encodes the SMN1 protein (survival motor neuron protein) with SEQ ID NO: 1, and includes the nucleic acid sequence of SEQ ID NO: 2.

The corresponding amino acid sequence of the SMN_HUMAN protein was used as a basis to produce the codon-optimized SMN1 gene:

```
                                          (SEQ ID NO: 1)
MAMSSGGSGGGVPEQEDSVLFRRGTGQSDDSDIWDDTALIKAYDKAVAS

FKHALKNGDICETSGKPKTTPKRKPAKKNKSQKKNTAASLQQWKVGDKC

SAIWSEDGCIYPATIASIDFKRETCVVVYTGYGNREEQNLSDLLSPICE

VANNIEQNAQENENESQVSTDESENSRSPGNKSDNIKPKSAPWNSFLPP

PPPMPGPRLGPGKPGLKFNGPPPPPPPPPPHLLSCWLPPFPSGPPIIPP

PPPICPDSLDDADALGSMLISWYMSGYHTGYYMGFRQNQKEGRCSHSLN
```

This amino acid sequence of SEQ ID NO:1 was translated into a nucleotide sequence by sequentially matching each amino acid starting from the N-end of one of the synonymous codons encoding same.

Detailed information on the codon-optimized SMN1 gene and the selection of a final sequence is provided in Example 1.

The final codon-optimized sequence of SMN1 (SMN1-GeneBeam) has the following nucleotide sequence:

```
                                          (SEQ ID NO: 2)
ATGGCCATGAGCAGCGGCGGCAGCGGCGGCGGCGTGCCTGAGCAAGAGG

ACAGCGTGCTGTTCAGAAGAGGCACCGGCCAGAGCGACGACAGCGACAT

CTGGGACGACACCGCCCTGATCAAGGCCTACGACAAGGCCGTGGCCAGC

TTCAAGCACGCCCTGAAGAACGGCGACATCTGCGAGACCAGCGGCAAGC

CCAAGACCACCCCCAAGAGAAAGCCCGCCAAGAAGAACAAGAGCCAGAA

GAAGAACACCGCCGCCAGCCTGCAGCAGTGGAAGGTGGGCGACAAGTGC

AGCGCCATCTGGAGCGAGGACGGCTGCATCTACCCCGCCACCATCGCCA

GCATCGACTTCAAGAGAGAGACCTGCGTGGTGGTGTACACCGGCTACGG

CAACAGAGAGGAGCAGAACCTGAGCGACCTGCTGAGCCCCATCTGCGAG

GTGGCCAACAACATCGAGCAGAACGCCCAAGAGAACGAGAACGAGAGCC

AAGTGAGCACCGACGAGAGCGAGAACAGCAGAAGCCCCGGCAACAAGAG

CGACAACATCAAGCCCAAGAGCGCCCCCTGGAACAGCTTCCTGCCCCCT

CCCCCCCCTATGCCCGGCCCTAGACTGGGCCCTGGCAAGCCTGGCCTGA

AGTTCAACGGCCCCCCCCCCCCCTCCTCCTCCTCCTCCTCCTCACCTGCT

GAGCTGCTGGCTGCCCCCCCTTCCCCAGCGGCCCTCCTATCATCCCTCCT

CCCCCCCCCCATCTGCCCCGACAGCCTGGACGACGCCGACGCCCTGGGCA

GCATGCTGATCAGCTGGTACATGAGCGGCTACCACACCGGCTACTACAT

GGGCTTCAGACAGAACCAGAAGGAGGGCCGGTGCAGCCACAGCCTGAAC

TAG.
```

This final codon-optimized nucleotide sequence of SMN1 (SMN1-GeneBeam) has an increased codon adaptation index (a standard measure for evaluating a sequence for codon frequencies) as compared to the coding sequence of the wild-type SMN gene (SMN1-WT):

```
                                          (SEQ ID NO: 3)
ATGGCGATGAGCAGCGGCGGCAGTGGTGGCGGCGTCCCGGAGCAGGAGG

ATTCCGTGCTGTTCCGGCGCGGCACAGGCCAGAGCGATGATTCTGACAT

TTGGGATGATACAGCACTGATAAAAGCATATGATAAAGCTGTGGCTTCA

TTTAAGCATGCTCTAAAGAATGGTGACATTTGTGAAACTTCGGGTAAAC

CAAAAACCACACCTAAAAGAAAACCTGCTAAGAAGAATAAAAGCCAAA

GAAGAATACTGCAGCTTCCTTACAACAGTGGAAAGTTGGGGACAAATGT

TCTGCCATTTGGTCAGAAGACGGTTGCATTTACCCAGCTACCATTGCTT

CAATTGATTTTAAGAGAGAAACCTGTGTTGTGGTTTACACTGGATATGG

AAATAGAGAGGAGCAAAATCTGTCCGATCTACTTTCCCCAATCTGTGAA

GTAGCTAATAATATAGAACAAAATGCTCAAGAGAATGAAAATGAAAGCC
```

-continued
```
AAGTTTCAACAGATGAAAGTGAGAACTCCAGGTCTCCTGGAAATAAATC

AGATAACATCAAGCCCAAATCTGCTCCATGGAACTCTTTTCTCCCTCCA

CCACCCCCCATGCCAGGGCCAAGACTGGGACCAGGAAAGCCAGGTCTAA

AATTCAATGGCCCACCACCGCCACCGCCACCACCACCACCCCACTTACT

ATCATGCTGGCTGCCTCCATTTCCTTCTGGACCACCAATAATTCCCCCA

CCACCTCCCATATGTCCAGATTCTCTTGATGATGCTGATGCTTTGGGAA

GTATGTTAATTTCATGGTACATGAGTGGCTATCATACTGGCTATTATAT

GGGTTTCAGACAAAATCAAAAAGAAGGAAGGTGCTCACATTCCTTAAAT

TAA.
```

The codon adaptation index for the final codon-optimized nucleotide sequence of the SMN1 gene (SEQ ID NO:2) is 98% for the subject sequence, and that is 75% for the wild-type sequence.

The GC content of the wild-type sequence is 45%, i.e. it differs from the target value by 15%, and the GC content of the final codon-optimized nucleotide sequence of the SMN1 gene (SEQ ID NO: 2) for the optimized sequence is 64%, i.e. it differs from the target value by 4%.

The final codon-optimized nucleotide sequence of the SMN1 gene (SEQ ID NO:2) and the nucleotide sequence of the wild-type SMN1 gene (SEQ ID NO:3) are identical by 71%.

Expression Cassette. Expression Vector.

In one aspect, the present invention relates to an expression cassette that includes the above codon-optimized nucleic acid.

The term "expression cassette", as used herein, refers in particular to a DNA fragment that is capable, in an appropriate setting, of inducing the expression of a polynucleotide encoding the polypeptide of interest that is included in said expression cassette. When introduced into a host cell, the expression cassette is, inter alia, capable of engaging cellular mechanisms to transcribe the polynucleotide encoding the polypeptide of interest into RNA that is then typically further processed and eventually translated into the polypeptide of interest. The expression cassette may be contained in an expression vector.

The expression cassette of the present invention comprises a promoter as an element. The term "promoter" as used herein refers in particular to a DNA element that promotes the transcription of a polynucleotide to which the promoter is operably linked. The promoter may further form part of a promoter/enhancer element. Although the physical boundaries between the "promoter" and "enhancer" elements are not always clear, the term "promoter" typically refers to a site on the nucleic acid molecule to which an RNA polymerase and/or any associated factors binds and at which transcription is initiated. Enhancers potentiate promoter activity temporally as well as spatially. Many promoters are known in the art to be transcriptionally active in a wide range of cell types. Promoters can be divided into two classes, those that function constitutively and those that are regulated by induction or derepression. The both classes are suitable for protein expression. Promoters that are used for high-level production of polypeptides in eukaryotic cells and, in particular, in mammalian cells, should be strong and preferably active in a wide range of cell types. Strong constitutive promoters which are capable of driving expression in many cell types are well known in the art and, therefore, it is not herein necessary to describe them in detail. In accordance with the idea of the present invention, it is preferable to use the cytomegalovirus (CMV) promoter. A promoter or promoter/enhancer derived from the immediate early (IE) region of human cytomegalovirus (hCMV) is particularly suitable as a promoter in the expression cassette of the present invention. The immediate early (IE) region of human cytomegalovirus (hCMV) and obtained therefrom functional expression-inducing fragments and/or functional expression-augmenting fragments, for example, are described in EP0173177 and EP0323997 and are also well known in the art. Thus, several fragments of the immediate early (IE) region of hCMV may be used as a promoter and/or promoter/enhancer. According to one embodiment of the invention, the human CMV promoter is used in the expression cassette of the present invention.

In some embodiments, the expression cassette includes the following elements in the 5'-end to 3'-end direction:

a left (first) ITR (inverted terminal repeats);

a CMV (cytomegalovirus) enhancer;

a CMV (cytomegalovirus) promoter;

an intron of the hBG1 gene (hemoglobin subunit gamma 1 gene)

the above codon-optimized nucleic acid of the SMN1 gene;

an hGH1 polyadenylation signal (human growth hormone gene polyadenylation signal) a right (second) ITR.

In some embodiments, the left (first) ITR (inverted terminal repeats) has the following nucleic acid sequence:

```
                                        (SEQ ID NO: 8)
Cctgcaggcagctgcgcgctcgctcgctcactgaggccgcccgggcgtc gggcgacctttggtcgcccggcctcagtgagcgagcgagcgcgcagaga gggagtggccaactccatcactaggggttcct.
```

In some embodiments, the CMV (cytomegalovirus) enhancer has the following nucleic acid sequence:

```
                                        (SEQ ID NO: 9)
cgttacataacttacggtaaatggcccgcctggctgaccgcccaacgac ccccgcccattgacgtcaataatgacgtatgttcccatagtaacgCcaa tagggactttccattgacgtcaatgggtggagtatttacggtaaactgc ccacttggcagtacatcaagtgtatcatatgccaagtacgcccctatt gacgtcaatgacggtaaatggcccgcctggcattatgcccagtacatga ccttatgggactttcctacttggcagtacatctacgtattagtcatcgc tattaccatg.
```

In some embodiments, the CMV (cytomegalovirus) promoter has the following nucleic acid sequence:

```
                                        (SEQ ID NO: 10)
gtgatgcggttttggcagtacatcaatgggcgtggatagcggtttgact cacggggatttccaagtctccaccccattgacgtcaatgggagtttgtt ttgGcaccaaaatcaacgggactttccaaaatgtcgtaacaactccgcc ccattgacgcaaatgggcggtaggcgtgtacggtgggaggtctatataa gcagagct.
```

In some embodiments, the intron of the hBG1 (hemoglobin subunit gamma 1) gene has the following nucleic acid sequence:

(SEQ ID NO: 11)
cgaatcccggccgggaacggtgcattggaacgcggattccccgtgccaa gagtgacgtaagtaccgcctatagagtctataggcccacaaaaaatgct ttcttcttttaatatacttttttgtttatcttatttctaatactttccc taatctctttctttcagggcaataatgatacaatgtatcatgcctcttt gcaccattctaaagaataacagtgataatttctgggttaaggcaatagc aatatttctgcatataaatatttctgcatataaattgtaactgatgtaa gaggtttcatattgctaatagcagctacaatccagctaccattctgctt ttattttatggttgggataaggctggattattctgagtccaagctaggc cctttttgctaatcatgttcatacctcttatcttcctcccacagctcctg ggcaacgtgctggtctgtgtgctggcccatcactttggcaaagaattgg gat.

In some embodiments, the hGH1 (human growth hormone 1 gene) polyadenylation signal has the following nucleic acid sequence:

(SEQ ID NO: 12)
Acgggtggcatccctgtgacccctccccagtgcctctcctggccctgga agttgccactccagtgcccaccagccttgtcctaataaaattaagttgc atcattttgtctgactaggtgtccttctataatattatggggtggaggg gggtggtatggagcaaggggcaagttgggaagacaacctgtagggcctg cggggtctattgggaaccaagctggagtgcagtggcacaatcttggctc actgcaatctccgcctcctgggttcaagcgattctcctgcctcagcctc ccgagttgttgggattccaggcatgcatgaccaggctcagctaattttt gtttttttggtagagacggggtttcaccatattggccaggctggtctcc aactcctaatctcaggtgatctacccaccttggcctcccaaattgctgg gattacaggcgtgaaccactgctcccttccctgtcctt.

In some embodiments, the right (second) ITR has the following nucleic acid sequence:

(SEQ ID NO: 13)
aggaacccctagtgatggagttggccactccctctctgcgcgctcgctc gctcactgaggccgggcgaccaaaggtcgcccgacgcccgggctttgcc cgggcggcctcagtgagcgagcgagcgcgcagctgcctgcagg.

In some embodiments, the expression cassette has the following nucleic acid sequence:

(SEQ ID NO: 4)
cctgcaggcagctgcgcgctcgctcgctcactgaggccgccgggcgtc gggcgacctttggtcgcccggcctcagtgagcgagcgagcgcgcagaga gggagtggccaactccatcactaggggttcctgcggccgcacgcgtcta gttattaatagtaatcaattacggggtcattagttcatagcccatatat ggagttccgcgttacataacttacggtaaatggcccgcctggctgaccg -continued
cccaacgacccccgcccattgacgtcaataatgacgtatgttcccatag taacgCcaatagggactttccattgacgtcaatgggtggagtatttacg gtaaactgcccacttggcagtacatcaagtgtatcatatgccaagtacg ccccctattgacgtcaatgacggtaaatggcccgcctggcattatgccc agtacatgaccttatgggactttcctacttggcagtacatctacgtatt agtcatcgctattaccatggtgatgcggttttggcagtacatcaatggg cgtggatagcggtttgactcacggggatttccaagtctccacccccattg acgtcaatgggagtttgttttgGcaccaaaatcaacgggactttccaaa atgtcgtaacaactccgccccattgacgcaaatgggcggtaggcgtgta cggtgggaggtctatataagcagagctcgtttagtgaaccgtcagatcg cctggagacgccatccacgctgtttgacctccatagaagacaccggga ccgatccagcctccgcggattcgaatcccggccgggaacggtgcattgg aacgcggattccccgtgccaagagtgacgtaagtaccgcctatagagtc tataggcccacaaaaaatgctttcttcttttaatatactttttttgttta tcttatttctaatactttccctaatctctttctttcagggcaataatga tacaatgtatcatgcctctttgcaccattctaaagaataacagtgataa tttctgggttaaggcaatagcaatatttctgcatataaatatttctgca tataaattgtaactgatgtaagaggtttcatattgctaatagcagctac aatccagctaccattctgcttttattttatggttgggataaggctggat tattctgagtccaagctaggcccttttgctaatcatgttcatacctctt atcttcctcccacagctcctgggcaacgtgctggtctgtgtgctggccc atcactttggcaaagaattgggattcgaacatCGATTGTAATTCATGAG

CCACCATGGCCATGAGCAGCGGCGGCAGCGGCGGCGGCGTGCCTGAGCA

AGAGGACAGCGTGCTGTTCAGAAGAGGCACCGGCCAGAGCGACGACAGC

GACATCTGGGACGACACCGCCCTGATCAAGGCCTACGACAAGGCCGTGG

CCAGCTTCAAGCACGCCCTGAAGAACGGCGACATCTGCGAGACCAGCGG

CAAGCCCAAGACCACCCCCAAGAGAAAGCCCGCCAAGAAGAACAAGAGC

CAGAAGAAGAACACCGCCGCCAGCCTGCAGCAGTGGAAGGTGGGCGACA

AGTGCAGCGCCATCTGGAGCGAGGACGGCTGCATCTACCCCGCCACCAT

CGCCAGCATCGACTTCAAGAGAGAGACCTGCGTGGTGGTGTACACCGGC

TACGGCAACAGAGAGGAGCAGAACCTGAGCGACCTGCTGAGCCCCATCT

GCGAGGTGGCCAACAACATCGAGCAGAACGCCCAAGAGAACGAGAACGA

GAGCCAAGTGAGCACCGACGAGAGCGAGAACAGCAGAAGCCCCGGCAAC

AAGAGCGACAACATCAAGCCCAAGAGCGCCCCCTGGAACAGCTTCCTGC

CCCCTCCCCCCCCTATGCCCGGCCCTAGACTGGGCCCTGGCAAGCCTGG

CCTGAAGTTCAACGGCCCCCCCCCCCCTCCTCCTCCTCCTCCTCCTCAC

CTGCTGAGCTGCTGGCTGCCCCCCCTTCCCCAGCGGCCCTCCTATCATCC

CTCCTCCCCCCCCCATCTGCCCCGACAGCCTGGACGACGCCGACGCCCT

GGGCAGCATGCTGATCAGCTGGTACATGAGCGGCTACCACACCGGCTAC

TACATGGGCTTCAGACAGAACCAGAAGGAGGGCCGGTGCAGCCACAGCC

-continued

```
TGAACTGATctagagtcgacctgcagaagcttgcctcgagcagcgctgc tcgagagatctacgggtggcatccctgtgacccctccccagtgcctctc ctggccctggaagttgccactccagtgcccaccagccttgtcctaataa aattaagttgcatcattttgtctgactaggtgtccttctataatattat ggggtggagggggggtatggagcaaggggcaagttgggaagacaacct gtagggcctgcggggtctattgggaaccaagctggagtgcagtggcaca atcttggctcactgcaatctccgcctcctgggttcaagcgattctcctg cctcagcctcccgagttgttgggattccaggcatgcatgaccaggctca gctaatttttgtttttttggtagagacggggtttcaccatattggccag gctggtctccaactcctaatctcaggtgatctacccaccttggcctccc aaattgctgggattacaggcgtgaaccactgctcccttccctgtccttc tgattttgtaggtaaccacgtgcggaccgagcggccgcaggaacccta gtgatggagttggccactccctctctgcgcgctcgctcgctcactgagg ccgggcgaccaaaggtcgcccgacgcccgggctttgcccgggcggcctc agtgagcgagcgagcgcgcagctgcctgcagg.
```

In one aspect, the present invention relates to an expression vector that includes the above codon-optimized nucleic acid or the above expression cassette.

In some embodiments, the vector is a plasmid, i.e., a circular double stranded piece of DNA into which additional DNA segments may be ligated.

In some embodiments, the vector is a viral vector, wherein additional DNA segments may be ligated into the viral genome.

In some embodiments, vectors are capable of autonomous replication in a host cell into which they are introduced (e.g. bacterial vectors having a bacterial origin site of replication and episomal mammalian vectors). In further embodiments, vectors (e.g. non-episomal mammalian vectors) can be integrated into the genome of a host cell upon introduction into a host cell, and thereby are replicated along with the host gene. Moreover, certain vectors are capable of directing the expression of genes to which they are operably linked. Such vectors are referred to herein as "recombinant expression vectors" (or simply, "expression vectors").

The expression vectors include plasmids, retroviruses, adenoviruses, adeno-associated viruses (AAV), plant viruses, such as cauliflower mosaic virus, tobacco mosaic virus, cosmids, YACs, EBV derived episomes, and the like. DNA molecules may be ligated into the vector such that transcriptional and translational control sequences within the vector serve their intended function of regulating the transcription and translation of the DNA. The expression vector and expression control sequences may be selected to be compatible with the expression host cell used. DNA molecules may be introduced into the expression vector by standard methods (e.g. ligation of complementary restriction sites, or blunt end ligation if no restriction sites are present).

The recombinant expression vector may also encode a signal peptide that facilitates the secretion of the protein of interest from a host cell. The gene of the protein of interest may be cloned into the vector such that the signal peptide is linked in-frame to the amino terminus of the protein of interest. The signal peptide may be an immunoglobulin signal peptide or a heterologous signal peptide (i.e. a signal peptide from a non-immunoglobulin protein).

In addition to the SMN1-GB gene of the present invention, the recombinant expression of the vectors of the present invention may carry regulatory sequences that control the expression of the SMN1-GB gene in a host cell. It will be understood by those skilled in the art that the design of an expression vector, including the selection of regulatory sequences, may depend on such factors as the choice of a host cell to be transformed, the level of expression of a desired protein, and so forth. Preferred control sequences for an expression host cell in mammals include viral elements that ensure high levels of protein expression in mammalian cells, such as promoters and/or enhancers derived from a retroviral LTR, cytomegalovirus (CMV) (such as a CMV promoter/enhancer), simian virus 40 (SV40) (such as a SV40 promoter/enhancer), adenovirus, (e.g. the major late promoter adenovirus (AdMLP)), polyomavirus and strong mammalian promoters such as native immunoglobulin promoter or actin promoter.

The term "control sequences" refers to DNA sequences necessary for the expression of an operably linked coding sequence in a particular host organism. The control sequences that are suitable for prokaryotes, for example, include a promoter, optionally an operator sequence and a ribosome binding site. Eukaryotic cells are known to utilize promoters, polyadenylation signals, and enhancers.

As used in the present description, the term "promoter" or "transcription regulatory sequence" or "regulatory sequence" refers to a nucleic acid fragment that controls the transcription of one or more coding sequences, and that is located upstream with respect to the direction of reading relative to the direction of transcription from the transcription initiation site of the coding sequence, and is structurally identified by the presence of a binding site for DNA-dependent RNA polymerase, transcription initiation sites and any other DNA sequences, including, but not limited to, transcription factor binding sites, repressor and activator protein binding sites, and any other sequences of nucleotides known to one of skill in the art that directly or indirectly regulate the level of transcription with said promoter. A "constitutive" promoter is a promoter that is active in most tissues under typical physiological and developmental conditions. An "inducible" promoter is a promoter that is physiologically or developmentally regulated, e.g. under the influence of a chemical inducer. A "tissue specific" promoter is only active in specific types of tissues or cells.

The terms "enhancers" or "enhancer" as used herein may refer to a DNA sequence that is located adjacent to the DNA sequence that encodes a recombinant product. Enhancer elements are typically located in a 5' direction from a promoter element or can be located downstream of or within a coding DNA sequence (e.g. a DNA sequence transcribed or translated into a recombinant product or products). Hence, an enhancer element can be located 100 base pairs, 200 base pairs, or 300 or more base pairs upstream of a DNA sequence that encodes a recombinant product, or downstream of said sequence. Enhancer elements may increase the amount of a recombinant product being expressed from a DNA sequence above the level of expression associated with a single promoter element. Multiple enhancer elements are readily available to those of ordinary skill in the art.

In addition to the above genes and regulatory sequences, recombinant expression vectors of the invention may carry additional sequences, such as sequences that regulate replication of a vector in host cells (e.g. origins of replication) and selectable marker genes. The selectable marker gene facilitates the selection of host cells into which a vector has been introduced (see e.g. U.S. Pat. Nos. 4,399,216, 4,634, 15
16

665 and 5,179,017). For example, the selectable marker gene typically confers resistance to medicinal agents, such as G418, hygromycin or methotrexate, on a host cell into which the vector has been introduced. For example, selectable marker genes include a dihydrofolate reductase (DHFR) gene (for use in dhfr-host cells during methotrexate selection/amplification), a neo gene (for G418 selection), and a glutamate synthetase gene.

The term "expression control sequence" as used in the present description refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include the promoter of ribosome binding site, and transcription termination sequences; in eukaryotes, typically, such control sequences include promoters and transcription termination sequences. The term "control sequences" is intended to include at least all components, the presence of which is essential for expression and processing, and can also include additional components, the presence of which is advantageous, for example, leader sequences and fusion partner sequences.

As used herein, the term "operably linked" refers to a linkage of polynucleotide (or polypeptide) elements in a functional relationship. A nucleic acid is "operably linked" when it is present in functional relationship conditions with another nucleic acid sequence. For example, a transcription regulatory sequence is operably linked to a coding sequence if it affects the transcription of said coding sequence. The term "operably linked" means that the DNA sequences being linked are typically contiguous and, where it is necessary to join two protein coding regions, are also contiguous and are present in the reading frame.

In one embodiment of the present invention, "expression vector" relates to a vector comprising one or more polynucleotide sequences of interest, genes of interest, or "transgenes" that are flanked by parvoviral sequences or inverted terminal repeat (ITR) sequences.

Neither the cassette nor the vector of the invention comprises nucleotide sequences of genes encoding non-structural proteins (Rep) and structural proteins (Cap) of the adeno-associated virus.

AAV9 (Adeno-Associated Virus Serotype 9)-Based Recombinant Virus

In one aspect, the present invention relates to an AAV9 (adeno-associated virus serotype 9)-based recombinant virus for increasing the expression of the SMN1 gene in target cells, which includes a capsid and the above expression cassette.

The term "AAV-based recombinant virus" (or "AAV-based virus-like particle", or "AAV recombinant virus strain", or "AAV recombinant vector", or "rAAV vector") as used in this description refers to the above expression cassette (or the above expression vector), which is enclosed within the AAV capsid.

The Cap gene, among other alternative products, encodes 3 capsid proteins (VP1, VP2, and VP3). VP1, VP2, and VP3 are present at 1:1:10 ratio to form an icosahedral capsid (Xie Q. et al. The atomic structure of adeno-associated virus (AAV-2), a vector for human gene therapy. Proc Natl Acad Sci USA, 2002; 99:10405-10410). Transcription of these genes starts from one promoter, p40. The molecular weights of the corresponding proteins (VP1, VP2 H VP3) are 87, 72, and 62 kDa, respectively. All of the three proteins are translated from a single mRNA. Following transcription, pre-mRNA may be spliced in two different manners, where either longer or shorter intron is excised to form mRNAs of various nucleotide lengths.

During the production of the AAV (rAAV)-based recombinant virus, an expression cassette flanked by ITR is packaged into an AAV capsid. The genes required for AAV replication, as mentioned above, are not included in the cassette.

The expression cassette DNA is packaged into a viral capsid in the form of a single stranded DNA molecule (ssDNA) being approximately 3000 nucleotides long. Once a cell is infected with the virus, the single-stranded DNA is converted to the form of double-stranded DNA (dsDNA). The dsDNA can only be used by the cell's proteins, which transcribe the present gene or genes into RNA.

In some embodiments, the AAV9-based recombinant virus has a capsid that includes the AAV9 protein VP1.

In some embodiments, the AAV9-based recombinant virus has a capsid that includes the AAV9 protein VP1 having the following amino acid sequence

```
                                          (SEQ ID NO: 5)
MAADGYLPDWLEDNLSEGIREWWALKPGAPQPKANQQHQDNARGLVLPG

YKYLGPGNGLDKGEPVNAADAAALEHDKAYDQQLKAGDNPYLKYNHADA

EFQERLKEDTSFGGNLGRAVFQAKKRLLEPLGLVEEAAKTAPGKKRPVE

QSPQEPDSSAGIGKSGAQPAKKRLNFGQTGDTESVPDPQPIGEPPAAPS

GVGSLTMASGGGAPVADNNEGADGVGSSSGNWHCDSQWLGDRVITTSTR

TWALPTYNNHLYKQISNSTSGGSSNDNAYFGYSTPWGYFDFNRFHCHFS

PRDWQRLINNNWGFRPKRLNFKLFNIQVKEVTDNNGVKTIANNLTSTVQ

VFTDSDYQLPYVLGSAHEGCLPPFPADVFMIPQYGYLTLNDGSQAVGRS

SFYCLEYFPSQMLRTGNNFQFSYEFENVPFHSSYAHSQSLDRLMNPLID

QYLYYLSKTINGSGQNQQTLKFSVAGPSNMAVQGRNYIPGPSYRQQRVS

TTVTQNNNSEFAWPGASSWALNGRNSLMNPGPAMASHKEGEDRFFPLSG

SLIFGKQGTGRDNVDADKVMITNEEEIKTTNPVATESYGQVATNHQSAQ

AQAQTGWVQNQGILPGMVWQDRDVYLQGPIWAKIPHTDGNFHPSPLMGG

FGMKHPPPQILIKNTPVPADPPTAFNKDKLNSFITQYSTGQVSVEIEWE

LQKENSKRWNPEIQYTSNYYKSNNVEFAVNTEGVYSEPRPIGTRYLTRN

L.
```

In some embodiments, the AAV9-based recombinant virus has a capsid that includes the AAV9 protein VP1 having the amino acid sequence of SEQ ID NO: 5 with one or more point mutations.

In some embodiments, the AAV9-based recombinant virus has a capsid that includes the AAV9 protein VP2.

```
                                          (SEQ ID NO: 6)
TAPGKKRPVEQSPQEPDSSAGIGKSGAQPAKKRLNFGQTGDTESVPDPQ

PIGEPPAAPSGVGSLTMASGGGAPVADNNEGADGVGSSSGNWHCDSQWL
```

-continued

```
GDRVITTSTRTWALPTYNNHLYKQISNSTSGGSSNDNAYFGYSTPWGYF

DFNRFHCHFSPRDWQRLINNNWGFRPKRLNFKLFNIQVKEVTDNNGVKT

IANNLTSTVQVFTDSDYQLPYVLGSAHEGCLPPFPADVFMIPQYGYLTL

NDGSQAVGRSSFYCLEYFPSQMLRTGNNFQFSYEFENVPFHSSYAHSQS

LDRLMNPLIDQYLYYLSKTINGSGQNQQTLKFSVAGPSNMAVQGRNYIP

GPSYRQQRVSTTVTQNNNSEFAWPGASSWALNGRNSLMNPGPAMASHKE

GEDRFFPLSGSLIFGKQGTGRDNVDADKVMITNEEEIKTTNPVATESYG

QVATNHQSAQAQAQTGWVQNQGILPGMVWQDRDVYLQGPIWAKIPHTDG

NFHPSPLMGGFGMKHPPPQILIKNTPVPADPPTAFNKDKLNSFITQYST

GQVSVEIEWELQKENSKRWNPEIQYTSNYYKSNNVEFAVNTEGVYSEPR

PIGTRYLTRNL.
```

In some embodiments, the AAV9-based recombinant virus has a capsid that includes the AAV9 protein VP2 having the amino acid sequence of SEQ ID NO: 6 with one or more point mutations.

In some embodiments, the AAV9-based recombinant virus has a capsid that includes the AAV9 protein VP3.

In some embodiments, the AAV9-based recombinant virus has a capsid that includes the AAV9 protein VP3 having the following amino acid sequence (SEQ ID NO: 7)
```
MASGGGAPVADNNEGADGVGSSSGNWHCDSQWLGDRVITTSTRTWALPT

YNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSD

YQLPYVLGSAHEGCLPPFPADVFMIPQYGYLTLNDGSQAVGRSSFYCLE

YFPSQMLRTGNNFQFSYEFENVPFHSSYAHSQSLDRLMNPLIDQYLYYL

SKTINGSGQNQQTLKFSVAGPSNMAVQGRNYIPGPSYRQQRVSTTVTQN

NNSEFAWPGASSWALNGRNSLMNPGPAMASHKEGEDRFFPLSGSLIFGK

QGTGRDNVDADKVMITNEEEIKTTNPVATESYGQVATNHQSAQAQAQTG

WVQNQGILPGMVWQDRDVYLQGPIWAKIPHTDGNFHPSPLMGGFGMKHP

PPQILIKNTPVPADPPTAFNKDKLNSFITQYSTGQVSVEIEWELQKENS

KRWNPEIQYTSNYYKSNNVEFAVNTEGVYSEPRPIGTRYLTRNL.
```

In some embodiments, the AAV9-based recombinant virus has a capsid that includes the AAV9 protein VP3 having the amino acid sequence of SEQ ID NO: 7 with one or more point mutations.

In some embodiments, the AAV9-based recombinant virus has a capsid that includes the AAV9 proteins VP1, VP2, and VP3.

In some embodiments, the AAV9-based recombinant virus has a capsid that includes the proteins VP1 with the amino acid sequence of SEQ ID NO: 5, VP2 with the amino acid sequence of SEQ ID NO: 6, and VP3 with the amino acid sequence of SEQ ID NO: 7.

In some embodiments, the AAV9-based recombinant virus has a capsid that includes the proteins VP1 with the amino acid sequence of SEQ ID NO: 5 with one or more point mutations, VP2 with the amino acid sequence of SEQ ID NO: 6 with one or more point mutations, and VP3 with the amino acid sequence of SEQ ID NO: 7 with one or more point mutations.

The phrase "more point mutations" refers to two, three, four, five, six, seven, eight, nine, or ten point substitutions.

Particularly preferred embodiments include substitutions (mutations) that are conservative in nature, i.e. substitutions that take place within a family of amino acids that are joined in their side chains. In particular, amino acids are typically divided into four families: (1) acidic amino acids are aspartate and glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. Phenylalanine, tryptophan, and tyrosine are sometimes classified as aromatic amino acids. For example, it is reasonably predictable that an isolated substitution of leucine for isoleucine or valine, an aspartate for a glutamate, a threonine for a serine, or a similar conservative substitution of an amino acid for a structurally related amino acid, will not have a major effect on the biological activity. For example, the polypeptide of interest may include up to about 5-10 conservative or non-conservative amino acid substitutions, so long as the desired function of the molecule remains intact.

An embodiment with point mutations in the sequences of AAV9 proteins VP 1, VP2, or VP3 using amino acid substitutions is a substitution of at least one amino acid residue in the AAV9 protein VP1, VP2, or VP3 with another amino acid residue.

Conservative substitutions are shown in Table A under "preferred substitutions".

TABLE A

| Original residue | Exemplary substitutions | Preferred substitutions |
|---|---|---|
| Ala (A) | Val; Leu; Ile | Val |
| Arg(R) | Lys; Gin; Asn | Lys |
| Asn(N) | Gin; His; Asp, Lys; Arg | Gin |
| Asp (D) | Glu; Asn | Glu |
| Cys (C) | Ser; Ala | Ser |
| Gln(Q) | Asn; Glu | Asn |
| Glu (E) | Asp; Gin | Asp |
| Gly(G) | Ala | Ala |
| His (H) | Asn; Gin; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gin; Asn | Arg |
| Met (M) | Leu; Phe; Ile | Leu |
| Phe(F) | Trp; Leu; Val; Ile; Ala; Tyr | Tyr |
| Pro (P) | Ala | Ala |
| Ser(S) | Thr | Thr |
| Thr (T) | Val; Ser | Ser |
| Trp(W) | Tyr; Phe | Ty |
| Tyr(Y) | Trp; Phe; Thr; Ser | Phe |
| Val (V) | Ile; Leu; Met; Phe; Ala; Norleucine | Leu |

In some embodiments, the AAV9-based recombinant virus has a capsid that includes the AAV9 protein VP1 having the amino acid sequence of SEQ ID NO: 5 or the amino acid sequence of SEQ ID NO: 5 with one or more point mutations, and the expression cassette includes the following elements in the 5'-end to 3'-end direction:

a CMV enhancer;
  a CMV promoter;
  an intron of the hBG1 gene;
  the above codon-optimized nucleic acid of the SMN1 gene;

an hGH1 polyadenylation signal;

a right ITR.

In some embodiments, the AAV9-based recombinant virus has a capsid that includes the proteins VP1 with the amino acid sequence of SEQ ID NO: 5, VP2 with the amino acid sequence of SEQ ID NO: 6, and VP3 with the amino acid sequence of SEQ ID NO: 7, and the expression cassette includes the following elements in the 5'-end to 3'-end direction:

a CMV enhancer;

a CMV promoter;

an intron of the hBG1 gene;

the above codon-optimized nucleic acid of the SMN1 gene;

an hGH1 polyadenylation signal;

a right ITR.

In some embodiments, the AAV9-based recombinant virus has a capsid that includes the proteins VP1 with the amino acid sequence of SEQ ID NO: 5 with one or more point mutations, VP2 with the amino acid sequence of SEQ ID NO: 6 with one or more point mutations, and VP3 with the amino acid sequence of SEQ ID NO: 7 with one or more point mutations, and the expression cassette includes the following elements in the 5'-end to 3'-end direction:

a CMV enhancer;

a CMV promoter;

an intron of the hBG1 gene;

the above codon-optimized nucleic acid of the SMN1 gene;

an hGH1 polyadenylation signal;

a right ITR.

In some embodiments, the AAV9-based recombinant virus has a capsid that includes the AAV9 protein VP1 having the amino acid sequence of SEQ ID NO: 5 or the amino acid sequence of SEQ ID NO: 5 with one or more point mutations, and the expression cassette comprises a nucleic acid with SEQ ID NO: 4.

In some embodiments, the AAV9-based recombinant virus has a capsid that includes the proteins VP1 with the amino acid sequence of SEQ ID NO: 5, VP2 with the amino acid sequence of SEQ ID NO: 6, and VP3 with the amino acid sequence of SEQ ID NO: 7, and the expression cassette comprises a nucleic acid with SEQ ID NO: 4.

In some embodiments, the AAV9-based recombinant virus has a capsid that includes the proteins VP1 with the amino acid sequence of SEQ ID NO: 5 with one or more point mutations, VP2 with the amino acid sequence of SEQ ID NO: 6 with one or more point mutations, and VP3 with the amino acid sequence of SEQ ID NO: 7 with one or more point mutations, and the expression cassette comprises a nucleic acid with SEQ ID NO: 4.

Pharmaceutical Composition

In one aspect, the present invention relates to a pharmaceutical composition for delivering the SMN1 gene to target cells, which includes the above AAV9-based recombinant virus in combination with one or more pharmaceutically acceptable excipients.

In particular embodiments, the present invention relates to a pharmaceutical composition comprising the AAV9-based recombinant virus of the invention in a pharmaceutically acceptable carrier or in other pharmaceutical agents, adjuvants, diluents, etc. For injection, the carrier will typically be a liquid carrier. For other methods of administration, the carrier may be either solid or liquid, such as sterile pyrogen-free water or sterile pyrogen-free phosphate-buffered saline solution. For inhalation administration, the carrier is respirable, and preferably is in a solid or liquid particulate form.

As an injection medium, it is preferred to use water that contains the additives that are common for injection solutions, such as stabilizing agents, salts or saline, and/or buffers.

"Pharmaceutical composition" means a composition comprising the above AAV9-based recombinant virus of the invention and at least one of components selected from the group consisting of pharmaceutically acceptable and pharmacologically compatible excipients, such as fillers, solvents, diluents, carriers, auxiliary, distributing agents, delivery agents, preservatives, stabilizers, emulsifiers, suspending agents, thickeners, prolonged delivery controllers, the choice and proportions of which depend on the type and route of administration and dosage. Pharmaceutical compositions of the present invention and methods for preparation thereof will be undoubtedly apparent to those skilled in the art. Pharmaceutical compositions should preferably be manufactured in compliance with the GMP (Good Manufacturing Practice) requirements. A composition may comprise a buffer composition, tonicity agents, stabilizers and solubilizers.

"Pharmaceutically acceptable" means a material that does not have biological or other negative side effects, for example, the material can be administered to a subject without causing any undesirable biological effects. Thus, such pharmaceutical compositions may be used, for example, in transfection of a cell ex vivo or in administration in vivo of the AAV9-based recombinant virus of the invention directly to a subject.

The term "excipient" is used herein to describe any ingredient other than the above ingredients of the invention. These are substances of inorganic or organic nature which are used in the pharmaceutical manufacturing in order to give drug products the necessary physicochemical properties.

"Stabilizer" refers to an excipient or a mixture of two or more excipients that provide the physical and/or chemical stability of the active agent.

The term "buffer", "buffer composition", "buffering agent" refers to a solution, which is capable of resisting changes in pH by the action of its acid-base conjugate components, which allows the rAAV5 vector product to resist changes in pH. Generally, the pharmaceutical composition preferably has a pH in the range from 4,0 to 8.0. Examples of buffers that can be used include, but are not limited to, acetate, phosphate, citrate, histidine, succinate, etc. buffer solutions.

A pharmaceutical composition is "stable" if the active agent retains physical stability and/or chemical stability and/or biological activity thereof during the specified shelf life at storage temperature, for example, of 2-8° C. Preferably, the active agent retains both physical and chemical stability, as well as biological activity. Storage period is adjusted based on the results of stability test in accelerated or natural aging conditions.

A pharmaceutical composition of the invention can be manufactured, packaged, or widely sold in the form of a single unit dose or a plurality of single unit doses in the form of a ready formulation. The term "single unit dose" as used herein refers to a discrete quantity of a pharmaceutical composition containing a predetermined quantity of an active ingredient. The quantity of the active ingredient typically equals the dose of the active ingredient to be administered in a subject, or a convenient portion of such dose, for example, half or a third of such dose.

Use

In one aspect, the present invention relates to the use of the above AAV9-based recombinant virus or the above composition to deliver the SMN1 gene to target cells.

Any method for administering the AAV9-based recombinant virus, which is recognized in the art, can be suitably used for the above AAV9-based recombinant virus of the present invention.

The AAV9-based recombinant virus is preferably administered to a cell in a biologically-effective amount. A "biologically-effective" amount of the recombinant virus is an amount that is sufficient to cause infection (or transduction) and expression of the heterologous nucleic acid sequence in the cell. If the virus is administered to a cell in vivo (e.g. the virus is administered to a subject, as described below), a "biologically-effective" amount of the viral vector is an amount that is sufficient to cause the transduction and expression of the heterologous nucleic acid sequence in the target cell.

The cell for administering the above AAV9-based recombinant virus of the invention may be a cell of any type, including but not limited to neural cells (including cells of the peripheral and central nervous systems, in particular, brain cells), lung cells, epithelial cells (e.g. gut and respiratory epithelial cells), muscle cells, pancreatic cells (including islet cells), hepatic cells, myocardial cells, bone cells (e.g. bone marrow stem cells), hematopoietic stem cells, spleen cells, keratinocytes, fibroblasts, endothelial cells, prostate cells, germ cells, and the like. Alternatively, the cell for administering the above AAV9-based recombinant virus may be any progenitor cell. As a further alternative, the cells may be stem cells (e.g. neural stem cells, liver stem cells). Furthermore, the cells may be from any species of origin, as specified above.

The above AAV9-based recombinant virus is not used to modify the genetic integrity of human germ line cells.

EXAMPLES

The following examples are provided for a better understanding of the invention. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended embodiments.

Materials and General Methods

Recombinant DNA Techniques

DNA manipulations were carried out by standard techniques as described by Sambrook J. et al, Molecular cloning: A laboratory manual; Cold Spring Harbor Laboratory Press, Cold Spring Harbor, New York, 1989. Molecular biological reagents were used according to the manufacturer instructions. Briefly, plasmid DNA was produced for further manipulation in *E. coli* cells grown under selective antibiotic pressure so that the plasmids were not lost in the cell population. We isolated the plasmid DNA from cells using commercial kits, measured the concentration, and used it for cloning by restriction endonuclease treatment or PCR amplification.

The DNA fragments were ligated to each other using ligases and transformed into bacterial cells for the selection of clones and further production. All resulting genetic constructs were confirmed by restriction patterns and complete Sanger sequencing.

Gene Synthesis

Desired gene segments were prepared from oligonucleotides made by chemical synthesis. Gene segments of 300 to 1000 bp long, which were flanked by unique restriction sites, were collected by renaturing oligonucleotides on top of each other, followed by PCR amplification from border primers. As a result, a mixture of fragments was produced, including the desired one. The fragments were cloned at restriction sites into intermediate vectors, following which the DNA sequences of the subcloned fragments were confirmed by DNA sequencing.

DNA Sequence Determination

DNA sequences were determined by Sanger sequencing. DNA and protein sequences were analyzed and sequence data was processed in SnapGene Viewer 4.2 or higher for sequence creation, mapping, analysis, annotation and illustration.

Culturing Cell Cultures

The experiments used HEK293 (Human Embryonic Kidney clone 293) and HSMC (Human Skeletal Muscle Cells) cell lines. The cells were cultured under standard conditions at 37° C. and 5% $CO_2$, on a DMEM complete culture medium supplemented with 10% FBS and an antibiotic. To culture HSMCs, the culture plastic was pre-coated with collagen (Gibco). Cells were subcultured upon reaching 80-90% confluence. Cell viability was assessed using either Trypan Blue stain and a hemocytometer or PI stain and flow cytometry.

Cell Transfection

Cell lines were inoculated the day before transfection into 6-well plates such that they reached 70-80% confluence by the time of transfection. Transfection was performed using commercial lipofection kits according to the manufacturer's protocol. After 72 h, the cells were treated with trypsin solutions or similar, removed from the substrate, washed in a phosphate buffer, and collected for further analysis of expression of target genes and proteins. For each transfection, a control plasmid expressing GFP was used to control the transfection efficiency (percentage of GFP-positive cells). Further analysis was performed only if the transfection efficiency was at least 50%.

All measurements were carried out in 3 independent experiments.

Gene Expression Analysis

SMN1 expression at the mRNA level was assessed by quantitative PCR. Briefly, primers and a sample specific for the wild-type SMN1 sequence or GeneBeam were used. Primers and a sample specific for the GAPDH housekeeping gene were used to control the initial RNA levels. Calibration curves were plotted for each set of primers and samples using a known copy number of linearized plasmid DNA comprising the amplified sequence of the corresponding gene. Expression was analyzed by determining, using the calibration curves, the copy number of SMN1-GeneBeam, SMN1-WT, and GAPDH in each sample, following which we normalized the copy number of SMN1 per 10,000 copies of GAPDH. The resulting values were compared for different samples within the same experiment.

Determination of SMN1 Protein Expression by Flow Cytometry

The SMN1 protein content in the cells was assessed by intracellular staining, followed by analysis using flow cytometry. Briefly, the cells were removed from culture plates using TrypLE, washed in PBS, fixed in a 4% paraformaldehyde solution, permeabilized using a 0.5% Triton X-100 solution in PBS, incubated in a blocking buffer supplemented with 1-5% BSA, and stained in two stages using primary antibodies to SMN1 and secondary antibodies labeled with Alexa Fluor 488. Following staining, the cells were washed once in PBS and analyzed on a flow cytometer. The average intensity of the signal was assessed after subtracting the signal stained with secondary antibodies without adding the primary antibodies.

Assembly and Purification of Viral Particles of Recombinant AAV Vectors

To assemble AAV particles containing the SMN1 gene or GFP control gene, we used HEK293 packaging cells, into which 3 plasmids were transfected as follows:

A plasmid comprising the AAV genome with a transgene (SNM1 or GFP) expression cassette;

A plasmid for expression of the AAV9 serotype Cap gene and the AAV2 serotype Rep gene. Each gene, using alternative reading frames, encodes several protein products;

A plasmid for expression of Ad5 (adenovirus serotype 5) genes that are required for assembly and packaging of AAV capsids.

After 72 hours, the cells were lysed and the viral particles were purified and concentrated using filtration and chromatography methods. The titer of the viral particles was determined by quantitative PCR with primers and a sample specific for the site of the recombinant viral genome and expressed as the copy number of viral genomes per 1 ml.

Transducing Cell Cultures

Cell lines were inoculated similarly to transfection experiments, following which the product with viral particles was added and the cells were analyzed after 72 hours. Transduction efficiency was estimated by measuring the percentage of GFP+ cells.

The cultures being used were pre-tested with the check of the transduction efficiency. Briefly, the AAV9-GFP viral product was transduced into the cell lines in different ratios of cells and viral particles. The ratio of viral particle number to cell number is referred to as multiplicity of infection (MOI). The MOI of the AAV9-GFP virus ranged from 50,000 to 1,000,000. As a result, MOI ranges, within which the transduction efficiency varied linearly depending on MOI, were determined for each line. Further transduction of cell lines was carried out within their linear ranges.

Following transduction, gene and protein expression was analysed as described above.

All measurements were carried out in 3 independent experiments.

Example 1. Method for Producing a Codon-Optimized SMN1 Gene

The corresponding amino acid sequence of the SMN_HUMAN protein (SEQ ID NO:1) was used as a basis to produce the codon-optimized SMN1 gene.

This amino acid sequence of SEQ ID NO:1 was translated into a nucleotide sequence by sequentially matching each amino acid starting from the N-end of one of the synonymous codons encoding same with the consideration of one or a combination of the following features:

1) frequency of codon usage (Yasukazu Nakamura ET AL., Codon usage tabulated from the international DNA sequence databases; its status 1999, Nucleic Acids Research, 1999, Vol. 27, No. 1, doi: 10.1093/nar/27.1.292);

2) GC content at the terminal region of the resulting nucleotide sequence (the target value of GC content was 60% as following from the article by Grzegorz Kudla ET AL., High Guanine and Cytosine Content Increases mRNA Levels in Mammalian Cells, PLoS Biol, June 2006, Volume 4, Issue 6, e180, doi: 10.1371/journal.pbio.0040180, so the smaller was the difference between the current GC content and the target one, the more preferable was the codon);

3) free energy of folding of the terminal region of the resulting nucleotide sequence (secondary structures were determined using the Zuker algorithm, Michael Zuker ET AL., Optimal computer folding of large RNA sequences using thermodynamics and auxiliary information, Nucleic Acids Research, Volume 9, Issue 1, 10 Jan. 1981, Pages 133-148, doi: 10.1093/nar/9.1.133).

The construction process further avoided the generation of semantic nucleotide sequences, such as restriction sites, internal ribosome entry sites, and splicing sites.

As a result of translating the amino acid sequence of SEQ ID NO: 1 to a nucleotide sequence, an array of codon-optimized nucleotide sequences of the SMN1 gene was produced.

Several sequences out of the above array of codon-optimized nucleotide sequences of SMN1 did not show an increase in SMN1 gene transcription in further studies, that is, there was no significant increase in the mRNA copy number of SMN1-opt as compared to SMN1-WT on any of the cell lines used, or this increase was insignificant.

Most of the codon-optimized nucleotide sequences of the SMN1 gene showed a 1.5-2-fold increase in the SMN1 gene transcription in further studies, that is, significantly increasing the mRNA copy number of SMN1-opt as compared to SMN1-WT on all the cell lines used.

One sequence out of the above array of codon-optimized nucleotide sequences of the SMN1 gene surprisingly showed more than 3-fold increase in the SMN1 gene transcription in further studies, that is, surprisingly increasing in the mRNA copy number of SMN1-opt by more than 3 times as compared to SMN1-WT on all the cell lines used (see Examples 3-4). This final codon-optimized nucleotide sequence of the SMN1 gene is conventionally called SMN1-GeneBeam (or abbreviated as SMN1-GB).

The final codon-optimized sequence of SMN1 (SMN1-GeneBeam) has a nucleotide sequence represented by SEQ ID NO: 2.

This final codon-optimized nucleotide sequence of SMN1 (SMN1-GeneBeam) is characterized by an increased codon adaptation index (Paul M. Sharp ET AL., The codon adaptation index-a measure of directional synonymous codon usage bias, and its potential applications, Nucleic Acids Research, Volume 15, Issue 3, 11 Feb. 1987, Pages 1281-1295, doi: 10.1093/nar/15.3.1281 —a standard measure for evaluating a sequence for codon usage frequencies) as compared to the coding sequence of the wild-type SMN gene (SMN1-WT with SEQ ID NO: 3).

The codon adaptation index for the final codon-optimized nucleotide sequence of the SMN1 gene (SEQ ID NO: 2) is 98%, and that for the wild-type sequence is 75%.

The GC content of the wild-type sequence is 45%, i.e. it differs from the target value by 15%, and that of the final codon-optimized nucleotide sequence of the SMN1 gene (SEQ ID NO: 2) is 64%, i.e. it differs from the target value by 4%.

The final codon-optimized nucleotide sequence of the SMN1 gene (SEQ ID NO:2) and the nucleotide sequence of the wild-type SMN1 gene (SEQ ID NO:3) are identical by 71%.

Example 2. Assembly of Genetic Constructs Carrying Recombinant AAV Genome and Encoding SMN1 Gene A wild-type SMN1 gene sequence was produced by amplification with specific primers with cDNA synthesized based on the total RNA of HEK293 cells. During the amplification process, the Kozak sequence and ClaI restriction site were added from the 5'-end of the gene, and the XbaI restriction site was added from the 3'-end. The sequence of the SMN1 gene was thereafter cloned by the restriction-ligase method at the ClaI and XbaI sites into A commercial construct pAAV-GFP Control plasmid (VPK-402) from CellBiolab (USA), with substitution of the GFP gene with SMN1, thereby producing the pAAV-SMN1-WT construct.

The SMN1-GeneBeam sequence was assembled as described above. In view of sequence complexity, despite its relatively small size, we performed a series of subcloning of gene fragments in intermediate vectors pGEMT, with sequence verification for each vector. Next, a full-length version of the gene was assembled from several intermediate vectors by PCR and cloned into the intermediate vector pGEMT. The construct pAAV-SMN1-WT was used as the final genetic construct, with substitution of the wild-type SMN1 with SMN1-GeneBeam at the ClaI and XbaI sites added to the ends of the SMN1-GeneBeam sequence by PCR.

The final vector contains all the necessary elements for expression and assembly of the gene as part of the recombinant AAV genome:

1) ITRs at the ends of the sequence that is encapsidated into a viral capsid;

2) Elements for expression of the target gene (promoter, enhancer, intron, Kozak sequence, transgene, polyadenylation site);

3) The bacterial replication origin and antibiotic resistance gene to produce plasmid DNA in bacterial cells.

It is important to note that the genetic constructs containing the SMN1-WT and SMN1-GeneBeam genes differ only in the SMN1 gene sequences, and are otherwise completely identical.

Example 3. Verification of SMN1 Expression from Genetic Constructs

The genetic constructs pAAV-GFP, pAAV-SMN1-WT, and pAAV-SMN1-GB were transfected into HEK293 cells and HSMCs as described above. We used 5 µg of DNA per 1 well. After 72 h, the cells were collected and the expression of SMN1 (normalized to GAPDH) was analyzed as described above.

It was found that the codon optimization of the SMN1 gene has an effect on the transcription of SMN1, reliably increasing by several times the mRNA copy number of SMN1-GB as compared to that of SMN1-WT on the both cell lines used (FIG. 1). In particular, for HEK293 cells, the normalized expression ratio of SMN1-GB to SMN1-WT was 3.9, whereas, for HSMCs, that was 12.8.

This property of SMN1-GeneBeam, as shown by the data obtained, is not cell-specific, and further provides a several-fold increased expression of the target gene in cells, which can be an important advantage in the development of gene-therapy drugs. Further, this property is not due to any differences in the gene expression cassette and to the properties of appropriate viral capsids carrying the genome from the SMN1-GeneBeam genes, since this analysis was performed on genetic constructs that differ only in the codon optimization of the SMN1 genes, and are otherwise completely identical.

Figure 2:
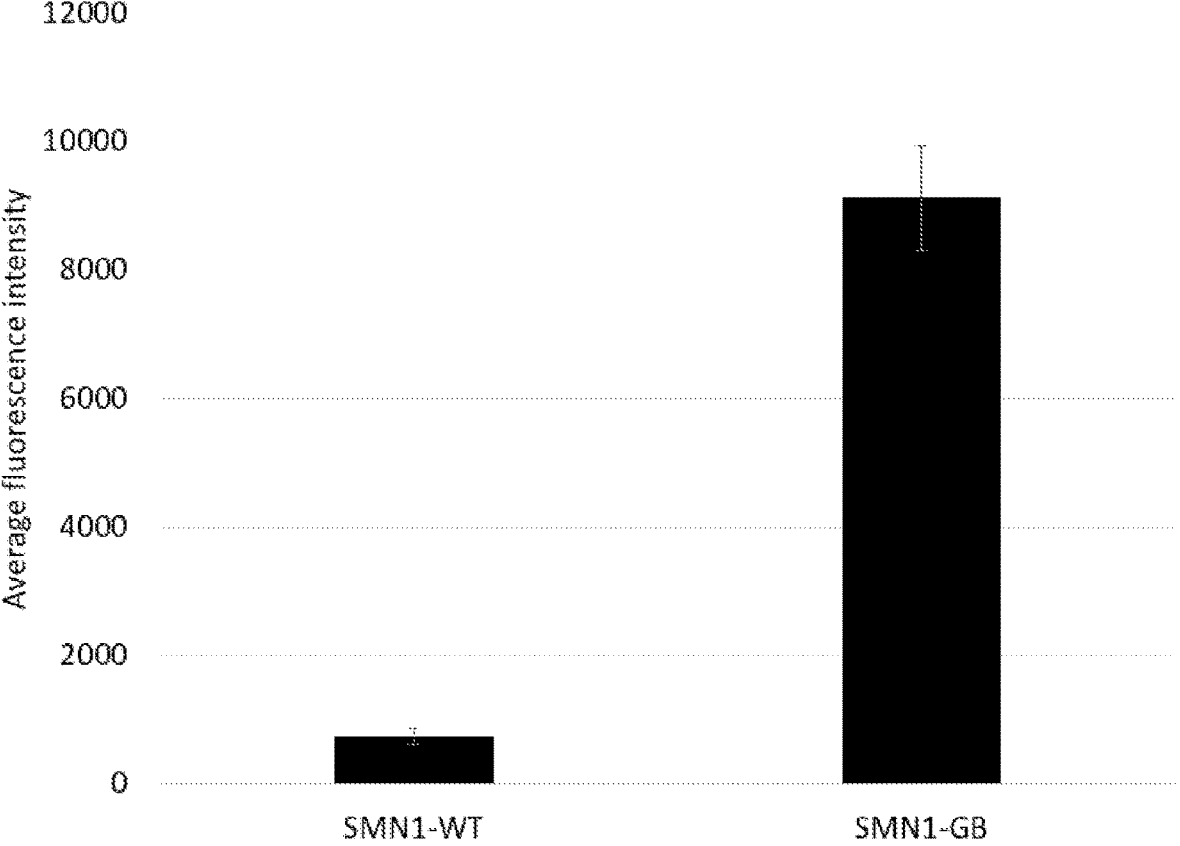
FIG. 2. SMN1 expression at the protein level following transfection. HSMCs were transfected with 5 μg of plasmids pAAV-SMN1-WT and pAAV-SMN1-GB (encoding the SMN1 gene without codon optimization and with codon optimization according to the GeneBeam algorithm). After 72 h, the cells were stained with primary antibodies to the SMN1 protein and secondary antibodies labeled with Alexa Fluor 488 in each sample (n=3). Shown is the average intensity of the fluorescent signal for living cells in the samples after subtracting the background signal obtained on cells stained with secondary antibodies without primary antibodies, with the indication of a standard deviation.

HSMCs were selected to check the expression of SMN1 at the protein level by flow cytometry, as described above. It was shown that the signal from SMN1-specific antibodies in cells transfected with pAAV-SMN1-GB is 12.2 times higher as compared to those transfected with pAAV-SMN1-WT at 5 µg of DNA used per 1 well (FIG. 2). This observation suggests that SMN1-GB has no advantages in translation, but the increased transcription further increases the final protein levels in the cells.

Example 4. Creating Viral Products Expressing SMN1

The plasmids pAAV-SMN1-WT and pAAV-SMN1-GB, along with other plasmids required to produce recombinant AAV viral particles (see above), were used for the bioprocess of AAV production. The serotype used was the wild-type AAV9 serotype or that with one or more point mutations.

In all cases, the properties of the wild-type SMN1 and SMN1-GeneBeam were compared only as long as the serotype used and capsid mutations, if any, were identical. All serotypes based on AAV9, either that of wild type or with mutations, are hereinafter referred to as AAV9 without specifying mutations.

The bioprocess produced recombinant viral particles designated as AAV9-SMN1-WT and AAV9-SMN1-GB, as well as control particles AAV9-GFP. After determining the titers of viral particles, all the 3 products with the same MOI (MOI values varied between experiments from 50,000 to 200,000) were used to transduce permissive cells, i.e. primary human myocytes HSMCs. Further analysis was performed only as long as the transduction efficiency was at least 50%.

Figure 3:
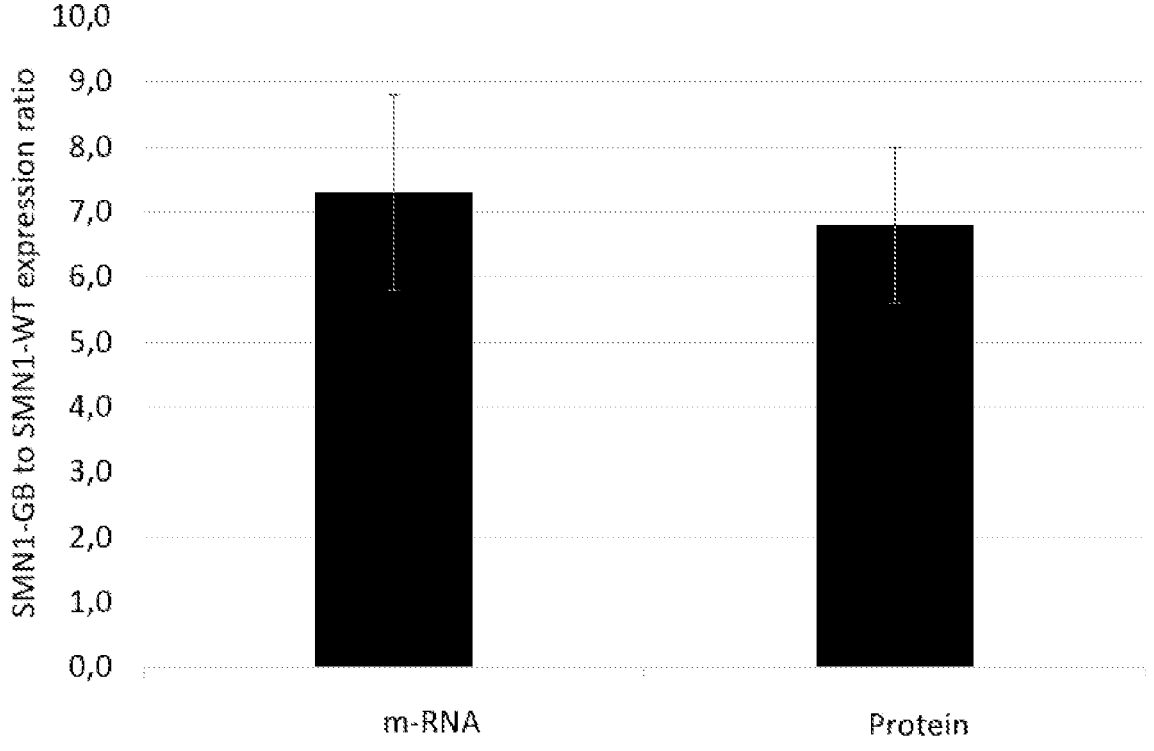
FIG. 3. The ratio of SMN1 expression at the mRNA and protein levels following transduction. HSMCs were transduced by AAV9-SMN1-WT and AAV9-SMN1-GB viruses in 3 independent experiments, in each of which the transduction efficiency was at least 50% for the control GFP-containing virus. SMN1 expression was determined at the mRNA and protein levels (see above), following which the ratio of SMN1-GB and SMN1-WT expression was calculated. The figure illustrates average ratios along with standard deviations.

Following successful transduction, the cells were removed from the substrate, washed in a phosphate buffer, and the expression of SMN1 was analyzed at the mRNA and protein levels as described above. The increased transcriptional activity of SMN1-GeneBeam was shown to remain consistent; thus, the mRNA of SMN1-GeneBeam was detected to be 7.3 times more than that of wild-type SMN1. A similar increase was further observed at the protein level (6.8 times) (FIG. 3), which shows that there are no advantages of SMN1-GB at the translation level; however, the detectable increase in transcription efficiency provides, using the AAV9-SMN1-GB product, a higher level of SMN1 expression in target cells, which is an important advantage in the treatment of, for example, spinal muscular atrophy, where the level of SMN1 protein expression defines the type of disease from 0 (embryonic lethality) to 4 (no special treatment required).

The invention claimed is:

1. A codon-optimized nucleic acid that encodes a SMN1 protein (survival motor neuron protein), the SMN1 protein comprising the amino acid sequence of SEQ ID NO: 1, the nucleic acid including the nucleic acid sequence of SEQ ID NO: 2.

2. An expression cassette that includes the codon-optimized nucleic acid of claim 1, including the following elements in the 5'-end to 3'-end direction:
    a left (first) ITR (inverted terminal repeats);
    a CMV (cytomeqalovirus) enhancer;
    a CMV (cytomeqalovirus) promoter;
    an intron of the hBG1 gene (hemoglobin subunit gamma 1 gene);
    the codon-optimized nucleic acid including the nucleic acid sequence of SEQ ID NO: 2;
    an hGH1 polyadenylation signal (human growth hormone gene polyadenylation signal); and
    a right (second) ITR.

3. The expression cassette of claim 2 that includes a nucleic acid comprising the nucleic acid sequence of SEQ ID NO: 4.

4. An expression vector that includes the codon-optimized nucleic acid of claim 1.

5. An AAV9 (adeno-associated virus serotype 9)-based recombinant virus for increasing the expression of the SMN1 gene in target cells, the AAV9-based recombinant virus including a capsid and the expression cassette of claim 2.

6. The AAV9-based recombinant virus of claim 5, wherein the capsid comprises the AAV9 protein VP1.

7. The AAV9-based recombinant virus of claim 6, wherein the capsid comprises the AAV9 protein VP1 having the amino acid sequence of SEQ ID NO: 5.

8. The AAV9-based recombinant virus of claim 6, wherein the capsid comprises the AAV9 protein VP1 having the amino acid sequence of SEQ ID NO: 5 with one or more point mutations.

9. The AAV9-based recombinant virus of claim 5, wherein the capsid comprises the AAV9 protein VP1 having the amino acid sequence of SEQ ID NO: 5 or the amino acid sequence of SEQ ID NO: 5 with one or more point mutations, and wherein the expression cassette includes the following elements in the 5'-end to 3'-end direction:

a CMV enhancer;

a CMV promoter;

an intron of the hBG1 gene;

the codon-optimized nucleic acid including the nucleic acid sequence of SEQ ID NO: 2;

an hGH1 polyadenylation signal; and a right ITR.

10. The AAV9-based recombinant virus of claim 5, wherein the capsid includes the AAV9 protein VP1 having the amino acid sequence of SEQ ID NO: 5 or the amino acid sequence of SEQ ID NO: 5 with one or more point mutations, and wherein the expression cassette includes a nucleic acid with SEQ ID NO: 4.

11. A pharmaceutical composition for delivering the SMN1 gene to target cells, including the AAV9-based recombinant virus of claim 5, in combination with one or more pharmaceutically acceptable excipients.

12. A method for delivering the SMN1 gene to one or more target cells comprising introducing the AAV9-based recombinant virus of claim 5 into the one or more target cells.

13. A method for delivering the SMN1 gene to one or more target cells comprising introducing the composition of claim 11 into the one or more target cells.

* * * * *